(12) United States Patent
Tashiro et al.

(10) Patent No.: US 9,493,497 B2
(45) Date of Patent: Nov. 15, 2016

(54) CARBAMATE GLYCOLIPID AND USE THEREOF

(71) Applicant: RIKEN, Wako-shi, Saitama (JP)

(72) Inventors: Takuya Tashiro, Wako (JP); Kenji Mori, Wako (JP); Masao Shiozaki, Wako (JP); Masaru Taniguchi, Wako (JP); Hiroshi Watarai, Wako (JP)

(73) Assignee: RIKEN, Wako (JP)

( * ) Notice: Subject to any disclaimer, the term of this patent is extended or adjusted under 35 U.S.C. 154(b) by 9 days.

(21) Appl. No.: 14/397,184

(22) PCT Filed: Apr. 26, 2013

(86) PCT No.: PCT/JP2013/062451
§ 371 (c)(1),
(2) Date: Oct. 25, 2014

(87) PCT Pub. No.: WO2013/162016
PCT Pub. Date: Oct. 31, 2013

(65) Prior Publication Data
US 2015/0152128 A1  Jun. 4, 2015

(30) Foreign Application Priority Data

Apr. 26, 2012  (JP) .................... 2012-101384

(51) Int. Cl.
*C07H 15/04* (2006.01)
*C07H 15/06* (2006.01)
*C12N 5/06* (2006.01)
*C12N 5/07* (2010.01)

(52) U.S. Cl.
CPC .............. *C07H 15/04* (2013.01); *C07H 15/06* (2013.01); *C12N 5/06* (2013.01)

(58) Field of Classification Search
None
See application file for complete search history.

(56) References Cited

U.S. PATENT DOCUMENTS

| | | |
|---|---|---|
| 6,531,453 B1 | 3/2003 | Taniguchi et al. |
| 8,283,163 B2 | 10/2012 | Inoue et al. |
| 8,853,173 B2 | 10/2014 | Tashiro et al. |
| 2003/0139351 A1 | 7/2003 | Taniguchi et al. |
| 2009/0162385 A1 | 6/2009 | Serra |
| 2009/0275483 A1* | 11/2009 | Wong ............... C40B 30/04 506/9 |
| 2010/0184214 A1 | 7/2010 | Inoue et al. |
| 2013/0005669 A1 | 1/2013 | Tashiro et al. |
| 2015/0210728 A1 | 7/2015 | Elewaut et al. |

FOREIGN PATENT DOCUMENTS

| | | |
|---|---|---|
| CN | 101755045 A | 6/2010 |
| WO | WO 98/44928 A1 | 10/1998 |
| WO | WO 03/105769 A2 | 12/2003 |
| WO | WO 2004/094444 A1 | 11/2004 |
| WO | WO 2007/118234 A2 | 10/2007 |
| WO | WO 2008/080926 A1 | 7/2008 |
| WO | WO 2010/023498 A1 | 3/2010 |
| WO | WO 2010/040710 A1 | 4/2010 |
| WO | WO 2011/096536 A1 | 8/2011 |
| WO | WO2014/001204 * | 1/2014 |
| WO | WO 2014/001204 A1 | 1/2014 |
| WO | WO 2014/133106 A1 | 9/2014 |

OTHER PUBLICATIONS

Aspeslagh et al., "Galactose-modified iNKT cell agonists stabilized by an induced fit of CD1d prevent tumour metastasis," *The EMBO Journal*, 30: 2294-2305 (2011).
Borg et al., "CD1d-lipid-antigen recognition by the semi-invariant NKT T-cell receptor," *Nature*, 448: 44-49 (2007).
Jervis et al., "Synthesis of a Versatile Building Block for the Preparation of 6-N-Derivatized α-Galactosyl Ceramides: Rapid Access to Biologically Active Glycolipids," *Journal of Organic Chemistry*, 76: 320-323 (2011).
Kawano et al., "CD1d-Restricted and TCR-Mediated Activation of $V_\alpha 14$ NKT Cells by Glycosylceramides," *Science*, 278: 1626-1629 (1997).
Li et al., "Identification of C-glycoside analogues that display a potent biological activity against murine and human invariant natural killer T cells," *Immunology*, 127: 216-225 (2008).

(Continued)

*Primary Examiner* — Traviss C McIntosh, III
(74) *Attorney, Agent, or Firm* — Leydig, Voit & Mayer, Ltd.

(57) ABSTRACT

The invention provides a compound effective as an antitumor active agent or vaccine adjuvant and an intermediate useful for the synthesis of the compound, as well as production methods thereof, and a medicament containing the novel compound. The compound is a carbamate glycolipid represented by the formula (I)

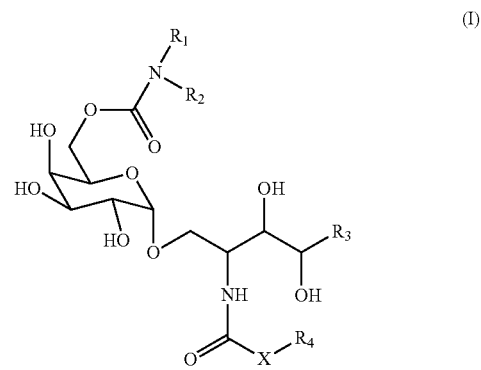

wherein each symbol is as defined herein. The invention also provides a dendritic cell pulsed with the glycolipid.

16 Claims, 11 Drawing Sheets

(56) References Cited

OTHER PUBLICATIONS

Li et al., "Design of a potent CD1d-binding NKT cell ligand as a vaccine adjuvant," *PNAS*, 107(29): 13010-13015 (Jul. 20, 2010).
Liang et al., "Quantitative Microarray Analysis of Intact Glycolipid-CD1d Interaction and Correlation with Cell-Based Cytokine Production," *Journal of American Chemical Society*, 130: 12348-12354 (2008).
Liu et al., "Synthesis of diglycosylceramides and evaluation of their iNKT cell stimulatory properties," *Bioorg. Med. Chem. Lett.*, 18(10): 3052-3055 (May 15, 2008).
Mallevaey et al., "T cell receptor CDR2β and CDR3β loops collaborate functionally to shape the iNKT cell repertoire," *Immunity*, 31(1): 60-71 (2009).
Scott-Browne et al., "Germline-encoded recognition of diverse glycolipids by natural killer T cells," *Nature Immunology*, 8(10): 1105-1113 (2007).
Trappeniers et al., "6'-Derivatised α-GalCer Analogues Capable of Inducing Strong CD1d-Mediated Th1-Biased NKT Cell Reponses in Mice," *Journal of American Chemical Society*, 130: 16468-16469 (2008).
Zhou et al., "Synthesis and NKT Cell Stimulating Properties of Fluorophore- and Biotin-Appended 6"-Amino-6"-deoxy-galactosylceramides," *Organic Letters*, 4(8): 1267-1270 (2002).
European Patent Office, Extended European Search Report in European Patent Application 13782299.5 (Sep. 9, 2015).
Japanese Patent Office, International Search Report in International Patent Application No. PCT/JP2013/062451 (Jul. 2, 2013) English translation.

* cited by examiner

CARBAMATE GLYCOLIPID AND USE THEREOF

CROSS-REFERENCE TO RELATED APPLICATIONS

This patent application is the U.S. national phase of International Patent Application No. PCT/JP2013/062451, filed Apr. 26, 2013, which claims the benefit of Japanese Patent Application No. 2012-101384, filed on Apr. 26, 2012, which are incorporated by reference in their entireties herein.

TECHNICAL FIELD

The present invention relates to a novel carbamate glycolipid and use thereof. More particularly, the present invention relates to a 6-carbamate glycolipid having carbamate at the 6-position of sugar, a production method thereof, and a pharmaceutical use thereof.

BACKGROUND ART

Immune system has a skillful surveillance function to distinguish abnormal cells from autochtonous normal cells in the body and eliminate only the abnormal cells. When the surveillance function collapses, abnormal cells produced by mutation and the like cannot be eliminated, and the presence and growth thereof in the body are allowed. The grown abnormal cell mass is a tumor, or cancer.

The cancer treatment is mainly removal of cancer by surgical operation, or use of anti-cancer agents. However, these treatment methods often place physical burden due to extirpative surgery and side effects of anti-cancer agents, or mental burden due to operative scar on patients.

With such background, treatments by immunotherapy are drawing attention. In the immunotherapy, the number of the patients' own immunocytes is increased, and further activated to attack the cancer cells. As compared to surgical operation, physical burden on the patients due to the treatment is small, and an influence on the patients' social life due to the treatment can be minimized. In addition, a treatment method using immunotherapy and a surgical operation in combination is also employed. Since a tumor minimized by immunotherapy can be removed, the physical burden on patients can be reduced. Also, since the operative scar is small, the mental burden can also be drastically reduced.

Natural killer (hereinafter NK) T cells are immunocytes belonging to a new lymphocyte lineage that exhibit characteristics different from those of other lymphocyte lineages (T, B, and NK cells). NKT cells are related to NK cells because cytotoxic perforin granules are present therein (non-patent document 1). However, because NKT cells express not only NK cell markers, but also T cell receptors (TCRs), they have been shown to represent a new class of cells that are completely different (non-patent document 2). NKT cells can produce both Th1 type cytokine [mainly interferon (IFN)-γ] produced by T helper (Th)1 cell that promotes immunostimulatory action, and Th2 type cytokine [mainly interleukin (IL)-4] produced by Th2 cell that promotes immunosuppressive action (non-patent document 3). In other words, NKT cells can induce both activation and quieting of the immune system, which suggests the possible role of the immune system in the balance adjustment (non-patent document 4). Therefore, when the function of NKT cells can be controlled, various diseases, particularly cancer, caused by abnormal balance of the immune system can be treated.

The characteristic of NKT cells that is attracting the greatest attention resides in the fact that the α chain of TCR expressed in NKT cells is the same in all the individuals belonging to one certain species. This essentially shows that all NKT cells of the same species of organism are activated by recognizing the same substance. As such, the α chain is Vα24 for humans and Vα14 for mice, there is a very high homology between the two species. For the βchain, which forms a pair with the α chain, only a very limited number of kinds are known, and therefore, this TCR is called "invariant TCR". It is also characteristic that TCR of NKT cells recognizes glycolipid, whereas TCR of T cells recognizes a protein fragment.

A wide variety of sphingoglycolipids are known to exist in living organisms. In general sphingoglycolipids in the living organisms, various sugars or sugar chains are bound to ceramides via β-bonds, and they are present in the cellular membranes of various organs.

Meanwhile, it is known that sphingoglycolipids comprising sugars bound to ceramides via α-bonds possess potent immunostimulatory action and antitumor activity. α-Galactosylceramides, typified by agelasphins, are glycolipids isolated from extracts from *Agelas mauritianus*, a kind of marine sponge, and have been reported to potently activate NKT cells (non-patent document 5). α-Galactosyl ceramides are taken by antigen presenting cells (APC) represented by dendritic cell (DC) and the like, and presented on a cellular membrane by CD1d protein similar to major histocompatibility complex (MHC) class I molecule. NKT cells are activated by recognizing a complex of the thus-presented CD1d protein and α-galactosylceramide by using TCR, whereby various immune reactions are initiated.

Heretofore, various analogs have been synthesized, and the correlation between the structure and the activity has been researched. It has been clarified that, among the series of synthetized analogs, KRN7000 (compound 1, α-GalCer) developed by Kirin Brewery Co., Ltd. shows an extremely strong anti-tumor activity, and the corresponding β-form (β-GalCer) does not show an immunostimulatory activity (patent document 1, non-patent document 6). KRN7000 is sphingoglycolipid comprising a ceramide resulting from the acylation of the sphingosine base by a long-chain fatty acid, and galactose bound thereto in α-configuration.

compound 1

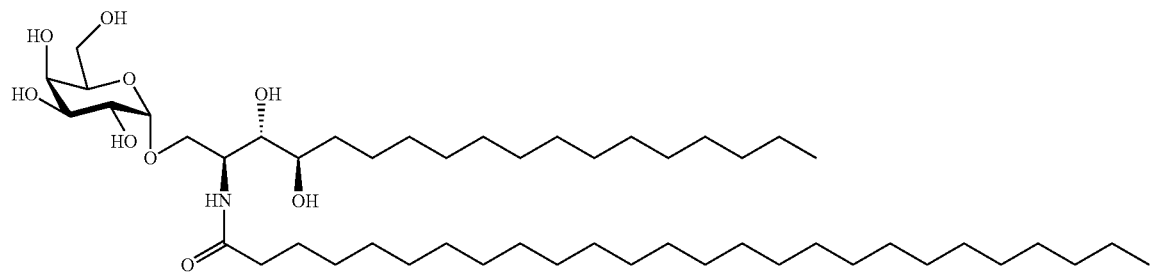

(KRN7000, α-GalCer)

In recent years, with a focus on the above-described functions of NKT cells, a therapeutic drug of cancer, which contains KRN7000 as an active ingredient, has been developed. However, NKT cells activated by the administration of KRN7000 produce IFN-γ, which is a cytokine useful for the cancer treatment and inducing immunostimulatory activity, as well as simultaneously produce IL-4, which is a cytokine inducing an immunosuppressive action. As a result, the effects of the both are cancelled by each other, posing the problem of lack of sufficient effect of cancer treatment.

The group of Tsuji et al. has developed a glycolipid, α-C-GalCer, that strongly activates NKT cells of mouse and preferentially produces IFN-γ (compound 2, patent document 2, non-patent document 7). However, since α-C-GalCer scarcely induces cytokine production in human NKT cells, its clinical application is considered to be difficult. To solve this problem, a compound that shows a strong activity also in the human system has been developed in recent years (non-patent document 8).

atom on the pyran ring and the 6-position hydroxyl group of sugar of KRN7000 do not form a hydrogen bond with any amino acid residue of CD1d or TCR.

On the other hand, we have separately developed that novel synthetic glycolipid RCAI-56 (compound 3) having carbasugar and found that the compound strongly activates NKT cells and induces production of a large amount of IFN-γ (non-patent document 10). We have further developed that novel synthetic glycolipid RCAI-61 (compound 4) wherein the 6-hydroxyl group of the sugar moiety of glycolipid is modified, and found that the compound is more easily prepared than RCAI-56 and induces production of IFN-γ in large amounts (non-patent document 11). Since RCAI-56 and RCAI-61 show strong activity even in the systems of mouse and human (in vitro), its clinical application is expected.

However, since the synthesis of RCAI-56 requires multiple steps, and the synthesis of RCAI-61 requires complicated modification of sugar, the development compound 2

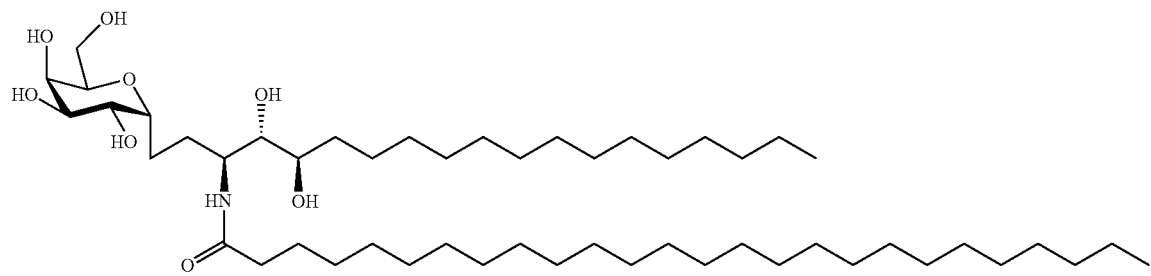

(α-C-GalCer)

A crystal structure analysis of human CD1d/KRN7000/TCR was reported in 2007 (non-patent document 9). According to the report, it has been clarified that the sugar moiety of KRN7000 is presented outside CD1d and towards TCR, whereas the ceramide moiety is stuck in a large hydrophobic pocket of CD1d. It was also found that oxygen of a novel analog permitting more convenient preparation and having an immunostimulatory activity equivalent to or higher than that of RCAI-56 and RCAI-61 has been desired. Furthermore, since RCAI-61 has a problem of low solubility in water, improvement of water solubility has been desired.

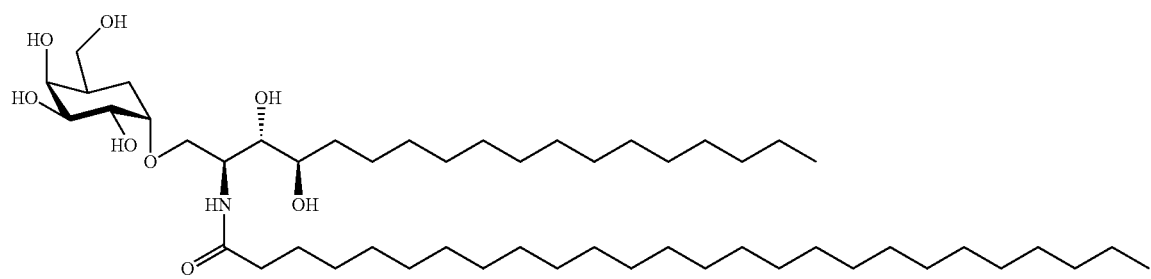

(RCAI-56) compound 3

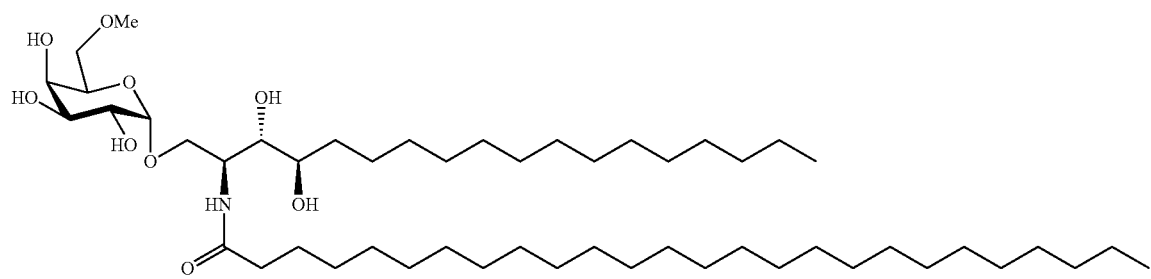

(RCAI-61) compound 4

In 2006, Savage et al. developed PBS-57 (compound 5) which is a glycolipid wherein the 6-position hydroxyl group of the sugar moiety of KRN7000 is converted to an acetamide group, and the compound shows improved solubility in DMSO, as well as a stronger activity than KRN7000 (non-patent document 12). It has been reported in recent years that the compound shows a strong adjuvant activity (patent documents 3-5). Moreover, Calenbergh et al. developed a glycolipid (compound 6) wherein the 6-position hydroxyl group of the sugar moiety of KRN7000 is converted to benzamide (non-patent document 13). Since benzamide analogs have a weak IL-4 production induction activity, they induce relatively largely polarized IFN-γ production. In any report, however, synthesis of analogs wherein the 6-position is converted to an amide group requires a step of converting the 6-position hydroxyl group to an explosive azido group. Therefore, the safety becomes a problem for industrial-scale synthesis.

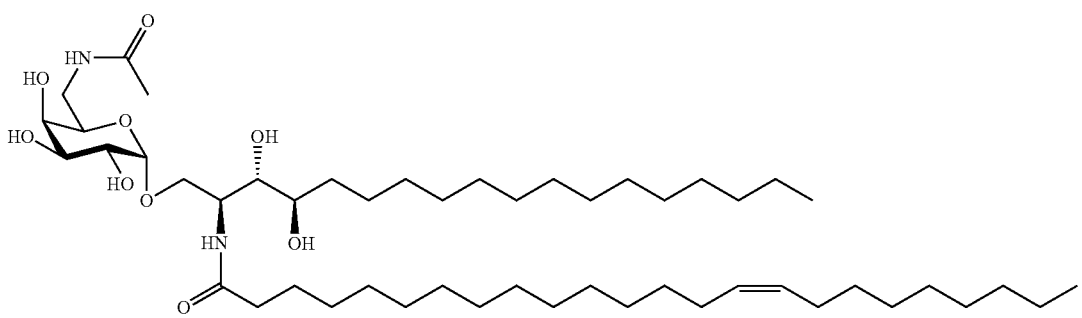

(PBS-57) compound 5

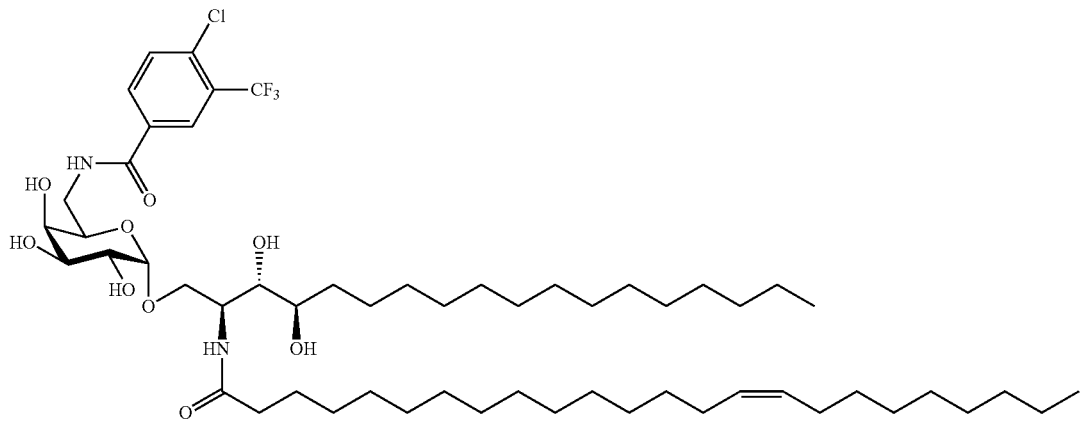

compound 6

A number of analogs wherein acyl side chain is modified rather than the sugar moiety have been synthesized, and the activity thereof has been investigated. In 2010, Wong et al. reported the development of an analog having an aromatic ring on the acyl side chain (non-patent document 14). It has been reported that a glycolipid, 7DW8-5 (compound 7), having enhanced affinity of ligand and CD1d due to a π-π stacking interaction with an amino acid residue having an aromatic ring in the inside of hydrophobic pocket of CD1d, shows a stronger adjuvant activity than KRN7000.

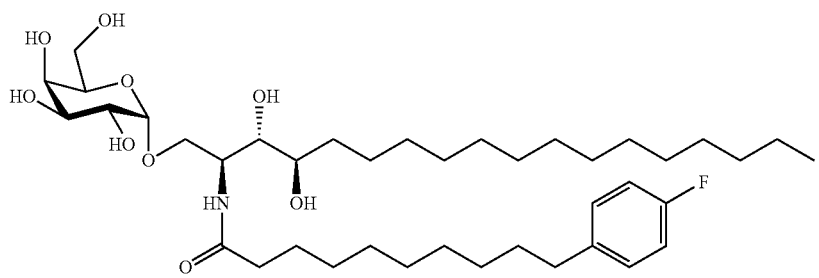

compound 7

(7DW8-5)

Patent document 6 and non-patent document 15 disclose, as KRN7000 derivative, a synthetic glycolipid having carbamate at the 6-position.

Besides these, there are many reports on the analogs wherein the 6-position hydroxyl group is converted to an amide bond (patent documents 7-9, non-patent documents 16-22).

DOCUMENT LIST

Patent Documents patent document 1: WO 98/44928
patent document 2: WO 03/105769
patent document 3: WO 2010/023498
patent document 4: WO 2010/040710
patent document 5: US-B-2009/0162385
patent document 6: US-B-2009/0275483
patent document 7: WO 2008/080926
patent document 8: WO 2007/118234
patent document 9: WO 2004/094444

Non-Patent Documents non-patent document 1: Proc. Natl. Acad. Sci. USA 1998, 95, 5690-5693
non-patent document 2: J. Immunol. 1995, 155, 2972-2983
non-patent document 3: J. Immunol. 1998, 161, 3271-3281
non-patent document 4: Science, 1997, 278, 1623-1626
non-patent document 5: Science, 1997, 278, 1626-1629
non-patent document 6: J. Med. Chem. 1995, 38, 2176-2187
non-patent document 7: J. Exp. Med. 2003, 198, 1631-1641
non-patent document 8: Immunology, 2009, 127, 216-225
non-patent document 9: Nature, 2007, 448, 44-49
non-patent document 10: Bioorg. Med. Chem. 2009, 17, 6360-6373
non-patent document 11: Tetrahedron Lett. 2008, 49, 6827-6830
non-patent document 12: J. Immunol. Method, 2006, 312, 34-39
non-patent document 13: J. Am. Chem. Soc., 2008, 130, 16468-16469
non-patent document 14: Proc. Natl. Acad. Sci. USA, 2010, 107, 13010-13015
non-patent document 15: J. Am. Chem. Soc., 2008, 130, 12348-12354
non-patent document 16: EMBO Journal, 2011, 30, 2294-2305 non-patent document 17: J. Org. Chem., 2011, 76, 320-323
non-patent document 18: Immunity 2009, 31, 60-71
non-patent document 19: Tetrahedron 2009, 65, 6390-6395
non-patent document 20: Bioorg. Med. Chem. Lett. 2008, 18, 3052-3055
non-patent document 21: Nature Immunol., 2007, 8, 1105-1113
non-patent document 22: Org. Lett., 2002, 4, 1267-1270

SUMMARY OF THE INVENTION

Problems to be Solved by the Invention

The present invention has been made in view of such actual condition, and its problem to be solved is provision of a novel compound effective as an antitumor active agent or a vaccine adjuvant and an intermediate useful for the synthesis of the compound and production methods thereof. In addition, it aims to provide a medicament which contains such novel compound.

Means of Solving the Problems

The present inventors have conducted studies in an attempt to solve the above-mentioned problems, and found that an analog wherein the 6-position hydroxyl group of the sugar moiety of glycolipid is converted to carbamate has a specific immunomodulatory potency, is extremely effective for the treatment of cancer and infection, and has a strong adjuvant activity, which resulted in the completion of the present invention.

Accordingly, the present invention provides the following.

[1] A compound represented by the formula (I)

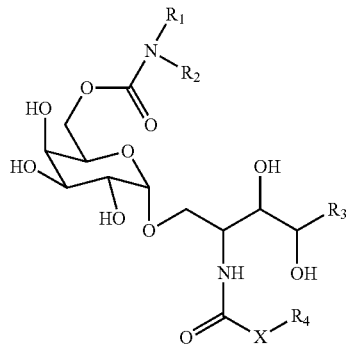

(I)

wherein
X is an alkylene group or —NH—;
$R_1$ and $R_2$ are the same or different and each is a hydrogen atom, an alkyl group, a hydroxyl group, an alkoxy group, or an aryl group optionally having substituent(s), $R_1$ and $R_2$ optionally form, together with the adjacent nitrogen atom, a 5- or 6-membered ring;
$R_3$ is a hydrocarbon group having 1-20 carbon atoms; and
$R_4$ is a hydrocarbon group having 1-30 carbon atoms, or a salt thereof.

[2] The compound of the above-mentioned [1], wherein X is methylene or —NH—, or a salt thereof.

[3] The compound of the above-mentioned [1], wherein $R_1$ is a hydrogen atom, a $C_{1-6}$ alkyl group, a hydroxyl group, a $C_{1-6}$ alkoxy group, or a $C_{6-12}$ aryl group optionally having substituent(s), or a salt thereof.

[4] The compound of the above-mentioned [1], wherein $R_2$ is a hydrogen atom, a $C_{1-5}$ alkyl group, a hydroxyl group, a $C_{1-6}$ alkoxy group, or a $C_{6-12}$ aryl group optionally having substituent(s), or a salt thereof.

[5] The compound of the above-mentioned [1], wherein the 5- or 6-membered ring optionally formed by $R_1$ and $R_2$ together with the adjacent nitrogen atom is a 5- or 6-membered nitrogen-containing saturated heterocycle, or a salt thereof.

[6] The compound of the above-mentioned [1], wherein $R_3$ is a $C_{1-20}$ alkyl group, a $C_{2-20}$ alkenyl group or a $C_{2-20}$ alkynyl group, or a salt thereof.

[7] The compound of the above-mentioned [1], wherein $R_4$ is a $C_{1-30}$ alkyl group, a $C_{2-30}$ alkenyl group or a $C_{2-30}$ alkynyl group, or a salt thereof.

[8] A medicament comprising the compound of any of the above-mentioned [1]-[7] or a salt thereof.

[9] A selective IFN-γ production inducer comprising the compound of any of the above-mentioned [1]-[7] or a salt thereof.

[10] A selective IFN-γ production inducer comprising the compound of any of the above-mentioned [1]-[7] or a salt thereof, which is pulsed on dendritic cells.

[11] A human dendritic cell pulsed with the compound of any of the above-mentioned [1]-[7] or a salt thereof.

[12] A selective IFN-γ production inducer comprising the human dendritic cell described in the above-mentioned [11].

[13] A compound represented by the formula (II)

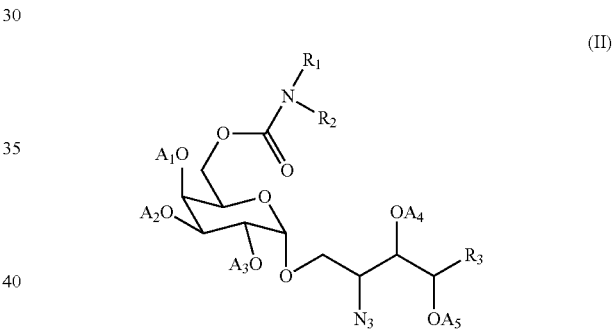

(II)

wherein
$A_1$-$A_5$ are the same or different and each is a hydroxyl-protecting group;
$R_1$ and $R_2$ are the same or different and each is a hydrogen atom, an alkyl group, a hydroxyl group, an alkoxy group, or an aryl group optionally having substituent(s), and $R_1$ and $R_2$ optionally form, together with the adjacent nitrogen atom, a 5- or 6-membered ring; and
$R_3$ is a hydrocarbon group having 1-20 carbon atoms, or a salt thereof.

[14] The compound of the above-mentioned [13], wherein $R_1$ and $R_2$ are the same or different and each is a hydrogen atom, a $C_{1-6}$ alkyl group, a hydroxyl group, a $C_{1-6}$ alkoxy group, or a $C_{6-12}$ aryl group optionally having substituent(s), and $R_1$ and $R_2$ optionally form, together with the adjacent nitrogen atom, a 5- or 6-membered nitrogen-containing saturated heterocycle, or a salt thereof.

[15] The compound of the above-mentioned [13], wherein $R_3$ is a $C_{1-20}$ alkyl group, a $C_{2-20}$ alkenyl group or a $C_{2-20}$ alkynyl group, or a salt thereof.

[16] A method of selectively inducing production of IFN-γ, comprising administering an effective amount of the compound of any of the above-mentioned [1]-[7] or a salt thereof to a target in need of the administration.

[17] A method of selectively inducing production of IFN-γ, comprising administering an effective amount of the compound of any of the above-mentioned [1]-[7] or a salt thereof to a target in need of the administration, and a step of pulsing dendritic cells with the compound or a salt thereof.

Effect of the Invention

An analog wherein the 6-position hydroxyl group of the sugar moiety of glycolipid is converted to alkylether, which is a hydrophobic functional group, has a problem of low solubility even though it induces IFN-γ polarized cytokine production rather than KRN7000. On the contrary, a carbamate group is more hydrophilic than an alkyl group. Furthermore, a hydroxyl group can be easily converted to a carbamate group. Unlike the amide group, use of a reagent or functional group having a risk of explosion is not necessary.

Therefore, since a glycolipid wherein the 6-position hydroxyl group of the sugar moiety is converted to a carbamate bond, which was developed by the present invention, can be synthesized highly easily and can induce IFN-γ polarized cytokine production rather than KRN7000, the present invention can provide a medicament effective for cancer treatment and induction of an adjuvant action, a production method thereof and use thereof.

Furthermore, IFN-γ production can be potentiated more by pulsing dendritic cells with the glycolipid of the present invention and administering the dendritic cells.

DESCRIPTION OF EMBODIMENTS

Figure 1:
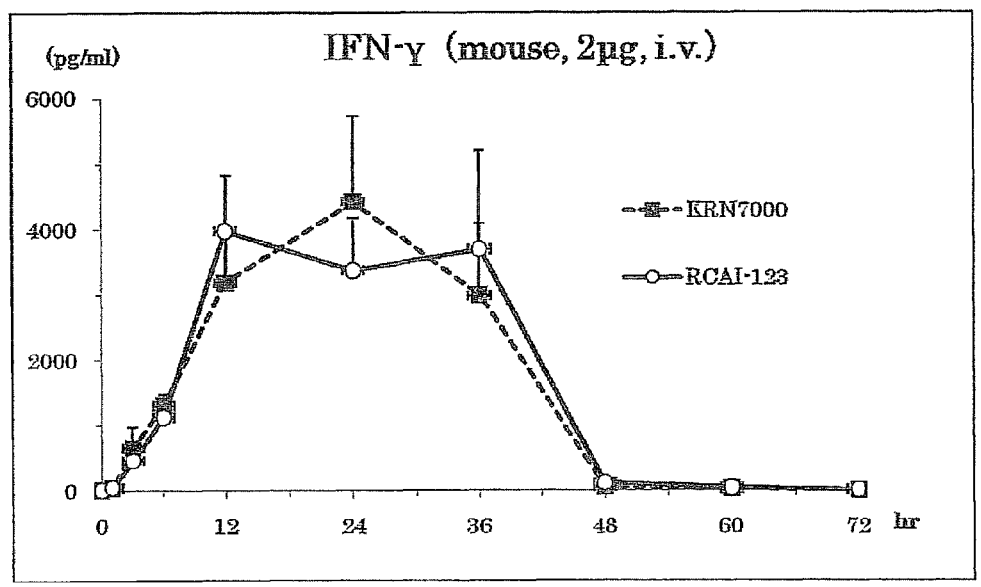
FIG. 1 is a graph showing changes in the IFN-γ concentration of mouse plasma after lapse of an indicated time after intravenous administration of a glycolipid (KRN7000 or RCAI-123) to mouse.

The present invention is explained in detail in the following by referring to preferable embodiments.

First, the definitions of the symbols to be used in each formula of the present specification are explained.

X is an alkylene group or —NH—. The "alkylene group" is, for example, a straight chain or branched alkylene group having 1-8 carbon atoms. Specific examples include methylene, ethylene, trimethylene, tetramethylene, pentamethylene, hexamethylene, heptamethylene, octamethylene, propylene, ethylethylene, dimethylmethylene, dimethyltrimethylene and the like.

$R_1$ and $R_2$ are the same or different and each is a hydrogen atom, an alkyl group, a hydroxyl group, an alkoxy group, or an aryl group optionally having substituent(s). $R_1$ and $R_2$ optionally form a 5- or 6-membered ring together with the adjacent nitrogen atom.

The "alkyl group" is, for example, a $C_{1-24}$, more preferably $C_{1-16}$, further preferably particularly preferably $C_{1-6}$ straight chain or branched alkyl group. Specific examples include methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl and the like. Preferred as the alkyl group for $R_1$ or $R_2$ is a $C_{1-6}$ alkyl group (e.g., methyl, ethyl).

The "alkoxy group" is, for example, a $C_{1-24}$, more preferably $C_{1-16}$, further preferably $C_{1-10}$, particularly preferably $C_{1-6}$, straight chain or branched alkoxy group. Specific examples include methoxy, ethoxy, propoxy, isopropoxy, butoxy, tert-butoxy and the like. Preferred as the alkoxy group for $R_1$ or $R_2$ is a $C_{1-6}$ alkoxy group (e.g., methoxy).

The "aryl group" in the "aryl group optionally having substituent(s)" is, for example, a $C_{6-14}$, more preferably $C_{6-12}$, monocyclic-tricyclic aryl group. Specific examples include phenyl, naphthyl, anthryl, phenanthryl and the like. Preferred as the aryl group for $R_1$ or $R_2$ is a $C_{6-12}$ aryl group (e.g., phenyl). Examples of the substituent that the "aryl group" optionally has include a halogen atom (e.g., chlorine atom, fluorine atom, bromine atom, iodine atom); an alkyl group (e.g., methyl, ethyl, n-propyl, isopropyl, n-butyl, isobutyl, sec-butyl, tert-butyl, pentyl, hexyl); a halogenoalkyl group (e.g., trifluoromethyl); an alkoxy group (e.g., methoxy, ethoxy, propoxy, isopropoxy, butoxy, tert-butoxy); a hydroxyl group; an amino group; an alkylamino group (e.g., methylamino, dimethylamino, ethylamino, diethylamino); a cycloalkylamino group and the like. The position and number of the substituents are not particularly limited, and one to substitutable maximum number of substituents may be present at substitutable position(s).

The 5- or 6-membered ring optionally formed by $R_1$ and $R_2$ together with the adjacent nitrogen atom is, for example, a 5- or 6-membered nitrogen-containing saturated heterocycle, which is specifically pyrrolidine, piperidine, morpholine, thiomorpholine, piperazine or the like. Preferred is pyrrolidine, piperidine or morpholine.

$R_3$ is a hydrocarbon group having 1-20 carbon atoms. The "hydrocarbon group having 1-20 carbon atoms" is a concept encompassing a $C_{1-20}$ alkyl group, a $C_{2-20}$ alkenyl group, a $C_{2-20}$ alkynyl group, a $C_{3-20}$ cycloalkyl group, a $C_{3-20}$ cycloalkenyl group, and even a $C_{6-20}$ aryl group, which may be linear, branched or cyclic, or may be a saturated hydrocarbon group or an unsaturated hydrocarbon group, and optionally having an unsaturated bond in a molecule or at the terminal. Among these, preferred as $R_3$ are a $C_{1-20}$ alkyl group, a $C_{2-20}$ alkenyl group, and a $C_{2-20}$ alkynyl group, and more preferred is a $C_{12-14}$ alkyl group. As $R_3$, specifically, —$C_{14}H_{29}$ and the like can be mentioned.

$R_4$ is a hydrocarbon group having 1-30 carbon atoms. The "hydrocarbon group having 1-30 carbon atoms" is a concept encompassing a $C_{1-30}$ alkyl group, a $C_{2-30}$ alkenyl group, a $C_{2-30}$ alkynyl group, a $C_{3-30}$ cycloalkyl group, a $C_{3-30}$ cycloalkenyl group, and even a $C_{6-30}$ aryl group, which may be linear, branched or cyclic, or may be a saturated hydrocarbon group or an unsaturated hydrocarbon group, and optionally has an unsaturated bond in a molecule or at the terminal. Among these, preferred as $R_4$ are a $C_{1-30}$ alkyl group, a $C_{2-30}$ alkenyl group, and a $C_{2-30}$ alkynyl group, more preferred is a $C_{10-30}$ alkyl group, and further preferred is a $C_{15-25}$ alkyl group. Specific examples of $R_4$ include $C_{16}H_{33}$, $C_{24}H_{49}$ and the like.

The hydrocarbon group for $R_3$ or $R_4$ optionally has substituent(s). When the hydrocarbon group for $R_3$ or $R_4$ has substituent(s), examples of the substituent include an electron-donating group such as a halogen atom (preferably chlorine atom, fluorine atom); an alkoxy group (preferably $C_{1-24}$, more preferably $C_{1-16}$, still more preferably $C_{1-10}$, particularly preferably $C_{1-4}$) such as methoxy, ethoxy, propoxy, isopropoxy, butoxy, tert-butoxy and the like; an aryloxy group (preferably $C_{6-14}$) such as phenoxy and the like; a hydroxyl group; an amino group; an alkylamino group such as methylamino, dimethylamino, ethylamino, diethylamino and the like; a cycloalkylamino group; an alkylcarbonylamino group such as acetamide and the like; a cycloalkylcarbonylamino group; arylcarbonylamino group (preferably, an arylcarbonylamino group wherein the aryl moiety is an aryl group having a carbon number of 6-14) such as benzoylamino and the like, and the like, further, an electron-withdrawing group such as a carboxyl group; an alkoxycarbonyl group; an acyl group (acyl group is as mentioned below, preferably an alkyl-carbonyl group wherein the alkyl moiety is a straight chain or branched alkyl group having a carbon number of 1 to 24); a carbamoyl group; trifluoromethyl and the like. The position and number of the substituents are not particularly limited, and one to substitutable maximum number of substituents may be present at substitutable position(s). When one or more substituents are present, they may be the same or different.

The "acyl group" in the present specification is, for example, a formyl group; an alkyl-carbonyl group (e.g., an alkyl-carbonyl group wherein the alkyl moiety is a straight chain or branched alkyl group having a carbon number of 1 to 24 (preferably 1 to 12) (e.g., acetyl, propionyl, butyryl, isobutyryl, valeryl, pivaloyl, hexanoyl)); a cycloalkyl-carbonyl group (e.g., a cycloalkyl-carbonyl group wherein the cycloalkyl moiety is a cycloalkyl group having a carbon number of 3 to 10); an alkenyl-carbonyl group (e.g., an alkenyl-carbonyl group wherein the alkenyl moiety is a straight chain or branched alkenyl group having a carbon number of 2 to 12 (e.g., acryloyl, methacryloyl)); an arylcarbonyl group (e.g., an aryl-carbonyl group wherein the aryl moiety is an aryl group having a carbon number of 6 to 14 (e.g., benzoyl, naphthoyl)) and the like. The aryl group of the aryl-carbonyl group is, for example, a monocyclic-tricyclic aromatic hydrocarbon group, and specific examples include phenyl, naphthyl, anthryl and phenanthryl. Of these, as the acyl group, formyl, acetyl, propionyl, butyryl, isobutyryl, benzoyl, naphthoyl and the like are preferable, and acetyl and benzoyl are more preferable.

Examples of the alkyl moiety of the above-mentioned alkylamino group and alkylcarbonylamino group include a straight chain or branched alkyl group (preferable carbon number 1-24, more preferable carbon number 1-16, still more preferable carbon number 1-10, particularly preferable carbon number 1-4) such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl and the like.

Examples of the cycloalkyl moiety of the above-mentioned cycloalkylamino group and cycloalkylcarbonylamino group include a cycloalkyl group (preferable carbon number 3-24, more preferable carbon number 3-16, still more preferable carbon number 3-10, particularly preferable carbon number 3-6) such as cyclopentyl, cyclohexyl and the like.

Examples of the alkoxy moiety of the above-mentioned alkoxycarbonyl group include those similar to the above-mentioned alkoxy group.

The above-mentioned substituents may be further substituted at substitutable position(s) by at least one kind from halogen, an alkyl group, a cycloalkyl group, an alkenyl group, an alkynyl group, a phenyl group, an alkoxy group, a hydroxyl group, an amino group, an alkylamino group and a cycloalkylamino group.

Examples of the halogen, alkoxy group, alkylamino group and cycloalkylamino group include those similar to the above.

Examples of the alkyl group include an alkyl group (preferable carbon number 1-24, more preferable carbon number 1-16, still more preferable carbon number 1-10, particularly preferable carbon number 1-4) such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl and the like.

Examples of the cycloalkyl group include a cycloalkyl group (preferable carbon number 3-24, more preferable carbon number 3-16, still more preferable carbon number 3-10, particularly preferable carbon number 3-6) such as cyclopentyl, cyclohexyl and the like.

Examples of the alkenyl group include an alkenyl group (preferable carbon number 2-24, more preferable carbon number 2-16, still more preferable carbon number 2-10, particularly preferable carbon number 2-4) such as vinyl, propenyl, butenyl and the like.

Examples of the alkynyl group include an alkynyl group (preferable carbon number 2-24, more preferable carbon number 2-16, still more preferable carbon number 2-10, particularly preferable carbon number 2-4) such as ethynyl, propargyl, butynyl, pentynyl and the like.

$A_1$-$A_5$ are the same or different and each is a hydrogen atom or a hydroxyl-protecting group. Examples of the "hydroxyl-protecting group" include benzyl, 4-methoxybenzyl (that is, p-methoxybenzyl (PMB)), methoxyethoxymethyl, tetrahydropyranyl, trimethylsilyl (TMS), t-butyldimethylsilyl (TBS or TBDMS), t-butyldiphenylsilyl (TBDPS), t-butoxycarbonyl, trichloroethoxycarbonyl, acetyl, pivaloyl and the like.

In the present invention, the α configuration is employed from among the stereoisomers derived from the cyclic structure of sugar (galactopyranose).

When compound (I) and compound (II) have a stereoisomer derived from a structure other than a cyclic structure of sugar (e.g., asymmetric carbon etc. of a part other than the cyclic structure of sugar), any isomers are also encompassed in the present invention, which may be a mixture (including racemate) of two or more kinds of isomers at any ratio.

Particularly, compound (I) contains an optical isomer derived from the asymmetric carbon of a part other than the cyclic structure of sugar. In the present invention, compound (I) may be a single optically active form or a mixture of two or more kinds of optically active forms at any ratio (including racemates). The asymmetric carbon to which —NHC(=O)X—$R^4$ is bonded is preferably in an S configuration, and the asymmetric carbon adjacent to the asymmetric carbon bonded to —NHC(=O)X—$R_4$, to which OH is bonded, is preferably in an R configuration. The asymmetric carbon to which $R_3$ is bonded is preferably in an R configuration.

In addition, compound (II) contains an optical isomer derived the asymmetric carbon of the part other than a cyclic structure of sugar. In the present invention, compound (II) may be a single optically active form or a mixture of two or more kinds of optically active forms at any ratio (including racemate). The asymmetric carbon to which $N_3$ is bonded is preferably in an S configuration. The asymmetric carbon to which —$OA_4$ is bonded is preferably in an R configuration. The asymmetric carbon to which —$OA_5$ is bonded is preferably in an R configuration.

Salts of compound (I) and compound (II) are preferably pharmacologically acceptable salts; examples include inorganic acid salts such as hydrochlorides, hydrobromides, hydroiodides, sulfates, nitrates, and phosphates; organic acid salts such as succinates, fumarates, acetates, methanesulfonates, and toluenesulfonates; alkali metal salts such as sodium salts and potassium salts; alkaline earth metal salts such as magnesium salts and calcium salts; ammonium salts such as ammonium salts and alkylammonium salts; and the like.

Specific examples of preferable compound (I) of the present invention are shown in Table 1, which is not to be construed as limitative.

TABLE 1

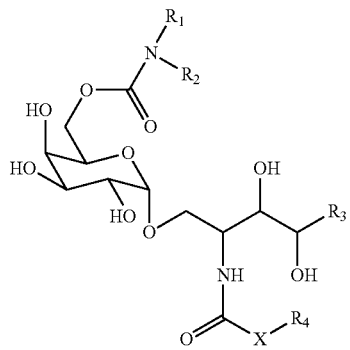

| | —$NR_1R_2$ | —X— | —$R_3$ | —$R_4$ |
|---|---|---|---|---|
| RCAI-123 | —$NMe_2$ | —$CH_2$— | —$C_{14}H_{29}$ | —$C_{24}H_{49}$ |
| RCAI-124 | —NHMe | —$CH_2$— | —$C_{14}H_{29}$ | —$C_{24}H_{49}$ |
| RCAI-137 | —NHOH | —$CH_2$— | —$C_{14}H_{29}$ | —$C_{24}H_{49}$ |
| RCAI-138 | —NHOMe | —$CH_2$— | —$C_{14}H_{29}$ | —$C_{24}H_{49}$ |
| RCAI-148 | —NHEt | —$CH_2$— | —$C_{14}H_{29}$ | —$C_{24}H_{49}$ |
| RCAI-149 | —$NEt_2$ | —$CH_2$— | —$C_{14}H_{29}$ | —$C_{24}H_{49}$ |
| RCAI-121 |  | | —$CH_2$— | —$C_{14}H_{29}$ | —$C_{24}H_{49}$ |
| RCAI-122 | 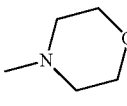 | | —$CH_2$— | —$C_{14}H_{29}$ | —$C_{24}H_{49}$ |
| RCAI-131 | 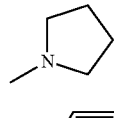 | | —$CH_2$— | —$C_{14}H_{29}$ | —$C_{24}H_{49}$ |
| RCAI-132 | 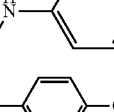 | | —$CH_2$— | —$C_{14}H_{29}$ | —$C_{24}H_{49}$ |
| RCAI-139 | 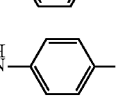 | | —$CH_2$— | —$C_{14}H_{29}$ | —$C_{24}H_{49}$ |
| RCAI-140 | 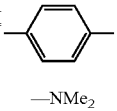 | | —$CH_2$— | —$C_{14}H_{29}$ | —$C_{24}H_{49}$ |
| RCAI-141 | 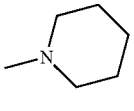 | | —$CH_2$— | —$C_{14}H_{29}$ | —$C_{24}H_{49}$ |
| RCAI-150 | —$NMe_2$ | —NH— | —$C_{14}H_{29}$ | —$C_{16}H_{33}$ |

The production method of compounds (I) and (II) of the present invention is explained below.

Compounds (I) and (II) can be produced according to the method described in the following scheme or a method analogous thereto, but the method is not limited thereto, and can be modified as appropriate on demand. Examples of such modification include alkylation, acylation, amination, imination, halogenation, reduction, oxidation and the like, for which reactions and methods generally used in the field are utilized. In this case, depending on the kind of the functional group, it is sometimes effective for production techniques to substitute the functional group in the stage of starting material or intermediate by a suitable protecting group (group easily convertible to the functional group). Chemical properties of protecting groups, method of introduction thereof, and removal thereof are described in detail in, for example, T. Greene and P. Wuts "Protective Groups in Organic Synthesis" (3$^{rd}$ ed.), John Wiley & Sons NY (1999).

As a starting material compound, unless particularly indicated, a commercially available product can be obtained easily, or can be produced according to a method known per se or a method analogous thereto.

The synthesis schemes of the compound of the present invention are shown below (detailed reactions follow Examples). In the schemes, specific groups and compounds are sometimes used for description. However, it is clear to those of ordinary skill in the art that alternative groups and compounds can be used.

Scheme 1

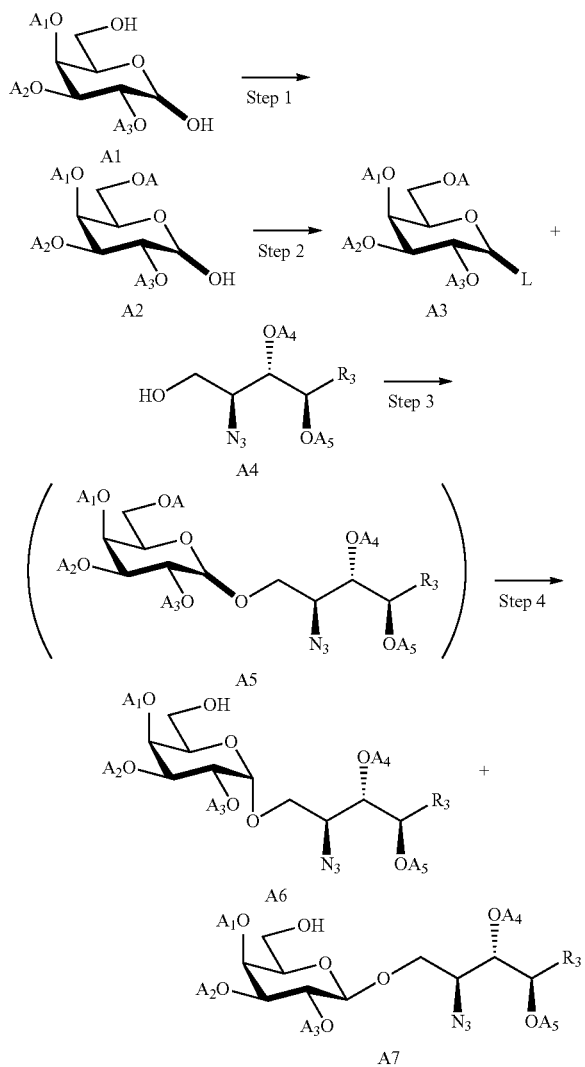

wherein A is a hydroxyl-protecting group, L is a leaving group, and other symbols are as defined above.

Examples of the hydroxyl-protecting group for A include those similar to the groups mentioned above for $A_1$-$A_5$. Examples of the leaving group for L include trichloroacetoimidoyloxy, phosphate [—OP(O)(OPh)$_2$ and the like], halogen (Br, F and the like) and the like.

[Step 1]

In Step 1, the 6-position hydroxyl group of compound A1 is protected. To be specific, compound A1 is reacted with a protecting reagent in an organic solvent in the presence of a base. Bases include amino compounds such as pyridine, 2,6-lutidine, triethylamine and the like. An organic silicon reagent is suitably used as the protecting reagent; for example, tert-butyldimethylsilyl trifluoromethanesulfonate, tert-butyldimethylsilyl chloride and the like can be used. The solvent may be any as long as it does not inhibit the reaction. As the solvent, N,N-dimethylformamide (DMF), tetrahydrofuran (THF), hexamethylphosphoric acid triamide (HMPA), a mixed solvent thereof and the like are used. The amount of the base to be used is generally 1-2 equivalents relative to compound A1. The amount of the protecting reagent to be used is generally 1-5 equivalents, preferably 1-2 equivalents, per one hydroxyl group of compound A1. The amount of the solvent to be used is generally 10-50-fold volume, preferably 10-20-fold volume, relative to compound A1. This step is preferably performed in the presence of a catalyst such as 4-(N,N-dimethylamino)pyridine (DMAP) and the like. The catalytic amount is sufficient as the amount of the catalyst to be used.

Reaction temperature is normally −20° C. to room temperature, preferably 0° C. to room temperature; reaction time is normally 1 to 48 hours, preferably 12 to 24 hours. After completion of the reaction, the reaction liquid is concentrated under reduced pressure, and the residue is purified by column chromatography, whereby compound A2 can be obtained in a high yield.

The starting material compound A1 can be synthesized by a method known from document (Carbohydr. Res., 1979, 73, 273).

[Step 2]

In Step 2, the 1-position hydroxyl group of compound A2 is converted to leaving group L to give compound A3. For example, when the leaving group is trichloroacetoimidoyloxy, compound A3 can be obtained by reacting compound A2 with trichloroacetonitrile in the presence of a base.

The amount of trichloroacetonitrile to be used is generally 1-10 equivalents relative to compound A2. Examples of the base include cesium carbonate, diazabicycloundecene (DBU), diazabicyclononene (DBN) and the like. The amount of the base to be used is generally 0.01-2 equivalents relative to compound A2. Examples of the solvent include dichloromethane, diethyl ether, THF and the like. The amount of the solvent to be used is generally 0.5-100 ml per 1 mmol of compound A2. The reaction temperature is generally 0-50° C., preferably room temperature, and the reaction time is generally 30 min-24 hr.

Compound A3 can be isolated by a conventional method. For example, compound A3 can be obtained by diluting with a solvent, washing with water, saturated aqueous sodium hydrogen carbonate solution, saturated brine and the like, drying over anhydrous potassium carbonate and the like, which is followed by filtration and concentration. Where necessary, further purification may be performed.

[Step 3]

In Step 3, compound A3 is reacted with compound A4 in the presence of trimethylsilyl trifluoromethanesulfonate and molecular sieves to give compound A5. The starting material compound A4 can be synthesized by a method known from document (Eur. J. Org. Chem., 1998, 291).

The amount of compound A3 to be used is generally 0.1-10 equivalents relative to compound A4. The amount of trimethylsilyl trifluoromethanesulfonate to be used is generally 0.01-3 equivalents relative to compound A3. The amount of the molecular sieves to be used is generally 1-2 g per 1 mmol of compound A3. Examples of the solvent include dichloromethane, trichloromethane, THF, dioxane, ethyl acetate and the like. The amount of the solvent to be used is generally 1-100 ml per 1 mmol of compound A3. The reaction temperature is generally −78-60° C., and the reaction time is generally 0.1-24 hr.

Compound A5 can be isolated by a conventional method. For example, after completion of the reaction, the reaction mixture is concentrated under reduced pressure, and the residue is purified by column chromatography, whereby compound A5 can be isolated.

[Step 4]

In Step 4, the 6-position hydroxyl-protecting group is deprotected. The deprotection method is selected from known methods according to the kind of the protecting group. For example, when protecting group A is a TBS group, compound A5 is reacted with tetrabutylammonium fluoride or an acid in a solvent.

As acid, a strong acid such as trifluoroacetic acid, p-toluenesulfonic acid, hydrochloric acid and the like is preferably used. The amount of the acid to be used is generally a catalytic amount to 10 equivalents, preferably 1 to 2 equivalents, relative to compound A5.

The amount of tetrabutylammoniumfluoride to be used is generally 2 equivalents-20 equivalents relative to compound A5.

The reaction temperature is generally −20 to 60° C., preferably room temperature, and the reaction time is generally 1-24 hr, preferably 2-12 hr.

Preferred as the solvent is a water-soluble solvent, and tetrahydrofuran is particularly preferable. The amount of the solvent to be used is generally 1-100-fold volume relative to compound A5.

After completion of the reaction, the reaction mixture is subjected to column chromatography using solvents with different polarity, whereby it is separated and purified into compound A6 (α-form) and compound A7 (β-form).

Scheme 2

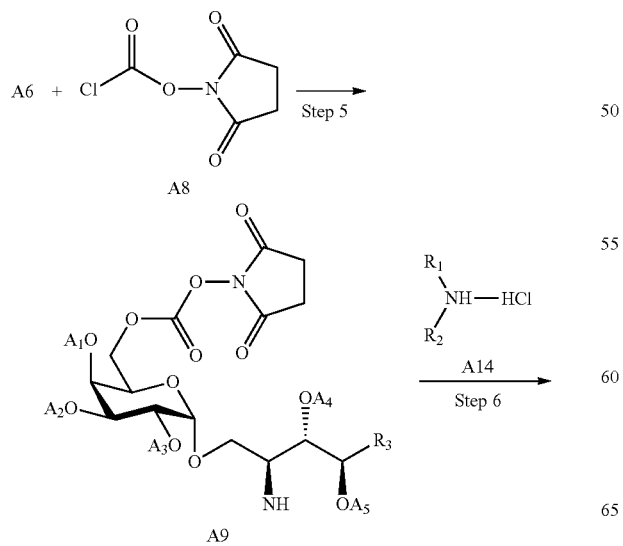

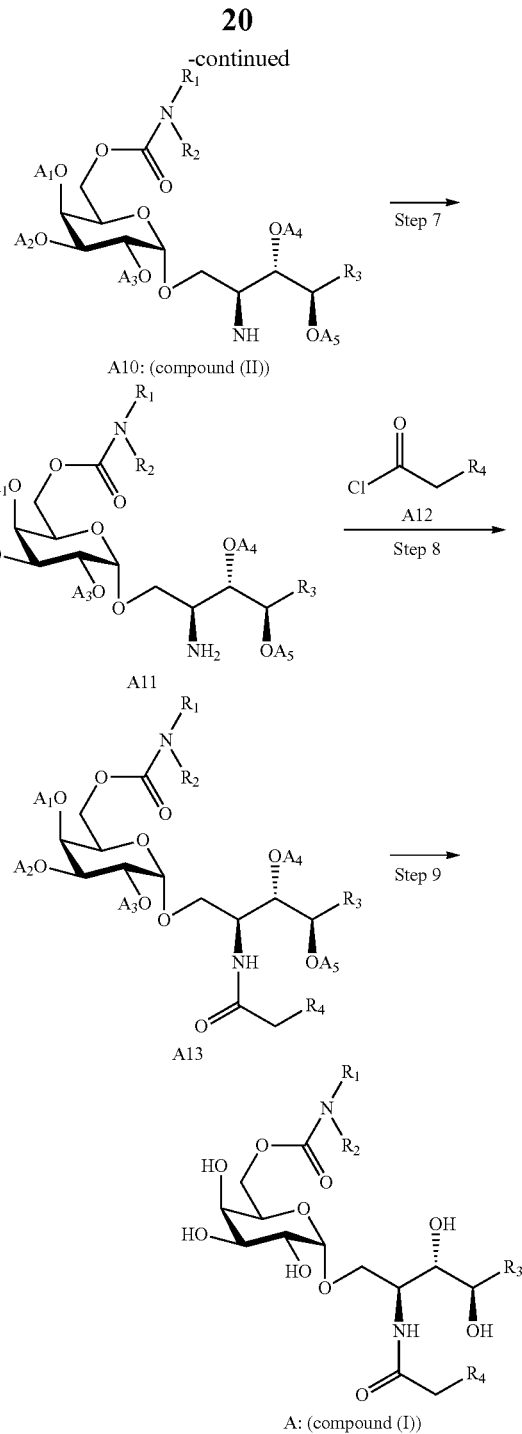

wherein each symbol is as defined above.

[Step 5]

In Step 5, in the presence of a base, compound A6 is reacted with compound A8 to give compound A9. The starting material compound A8 can be synthesized by a method known from document (Synthesis, 1993, 103).

The amount of compound A8 to be used is generally 1-10 equivalents, preferably 1-5 equivalents, relative to compound A6.

Examples of the base include pyridine, triethylamine and the like, and pyridine is preferable. The amount of the base to be used is generally 1-10 equivalents relative to compound A6. Any solvent can be used as long as it does not inhibit the reaction, and as the solvent, N,N-dimethylformamide (DMF), tetrahydrofuran (THF), hexamethylphosphoric acid triamide (HMPA), a mixed solvent thereof and the like are used. A mixed solvent of THF and DMF is preferable. The amount of the solvent to be used is generally 0.5-100 ml per 1 mmol of compound A6. The reaction temperature is −20° C. to room temperature, preferably 0-4° C., and the reaction time is generally 30 min-24 hr. After completion of the reaction, the reaction mixture is concentrated under reduced pressure, and the residue is purified by column chromatography to give compound A9 in a high yield.

[Step 6]

In Step 6, compound A9 is reacted with compound A14 in the presence of a base to give compound A10. Compound A10 is encompassed in compound (II). The starting material compound A14 varies depending on $R_1$ and $R_2$, and can be generally synthesized by a method known from document or is commercially available.

The amount of compound A14 to be used is generally 1-10 equivalents, preferably 2 equivalents, relative to compound A9.

Examples of the base include 4-(dimethylamino)pyridine (DMAP), diisopropylethylamine, DABCO and the like. The amount of the base to be used is generally 1-10 equivalents, preferably 5 equivalents, relative to compound A9. Examples of the solvent include N,N-dimethylformamide (DMF), THF, HMPA, a mixed solvent thereof and the like. The amount of the solvent to be used is generally 0.5-50 ml per 1 mmol of compound A9. The reaction temperature is generally −20-60° C., preferably room temperature, and the reaction time is generally 10 min-24 hr. After completion of the reaction, the reaction mixture is concentrated under reduced pressure, and the residue is purified by column chromatography to give compound A10 in a high yield.

[Step 7]

In Step 7, the azide group in compound A10 is converted to an amino group by reduction to give compound A11. To be specific, compound A10 is reacted with a reducing agent, and then with a base in an organic solvent. Examples of the reducing agent include phosphine compounds such as trimethylphosphine, tributylphosphine, triphenylphosphine and the like. As the solvent, any solvent can be used as long as it does not inhibit the reaction. For example, N,N-dimethylformamide (DMF), tetrahydrofuran (THF), hexamethylphosphoric acid triamide (HMPA), a mixed solvent thereof and the like are used. The amount of the reducing agent to be used is generally 1-5 equivalents, preferably 1-2 equivalents, per one azide group of compound A10. The reaction temperature is generally −20 to 60° C., preferably room temperature, and the reaction time is generally 1-48 hr, preferably 12-24 hr. After completion of the reaction, the reaction mixture is treated with a basic aqueous solution such as aqueous sodium hydroxide solution and the like, and compound A11 can be isolated and purified by a conventional method. For example, the compound is extracted with a solvent such as ethyl acetate and the like. The organic layer obtained is washed with a saturated aqueous solution of sodium hydrogen carbonate, saturated saline and the like, and dried with anhydrous potassium carbonate and the like. After the solution is filtered, the filtrate is concentrated under reduced pressure, and the residue may be purified by column chromatography.

[Step 8]

In Step 8, the amino group of compound A11 is acylated to give compound A13. To be specific, compound A11 is reacted with compound A12 in a solvent and, where necessary, in the presence of a base. Compound A12 (starting material compound) can be synthesized by a method known from document (Org. Lett., 2006, 8, 3375).

While the solvent is not particularly limited as long as the reaction is not inhibited, for example, halogen solvents (e.g., dichloromethane, chloroform) are preferably used.

Where necessary, a base may be added. Examples of the base include pyridine, triethylamine and the like, and triethylamine is preferable.

The amount of the solvent to be used is generally 5- to 100-fold volume, preferably 20- to 50-fold volume, relative to compound A11.

The amount of the base to be used is generally 10 to 50 equivalents, preferably 10 to 20 equivalents, relative to compound A11.

The amount of compound A12 to be used is generally 1 to 20 equivalents, preferably 1 to 2 equivalents, relative to compound A11.

The reaction temperature is generally −20° C. to room temperature, preferably 0 to 4° C., and the reaction time is generally 1 to 24 hr, preferably 6 to 12 hr.

After completion of the reaction, compound A13 can be isolated and purified by a conventional method. For example, the reaction mixture is diluted with water, and extracted with an ether solvent such as diethyl ether and the like, an ester solvent such as ethyl acetate and the like. When pyridine is used as a base, the obtained organic layer is washed with saturated aqueous copper sulfate solution, washed with water, saturated brine etc., and dried over anhydrous magnesium sulfate etc. After filtration, the filtrate is concentrated under reduced pressure, and the residue is purified by column chromatography and the like to give compound A13.

[Step 9]

In Step 9, the hydroxyl-protecting groups $A_1$-$A_5$ of compound A13 are deprotected to give compound A (compound (I)). The deprotection method is selected from known methods according to the kind of the protecting group. For example, in the case of a benzyl group, compound A13 is reacted in a solvent in the presence of hydrogen and a reduction catalyst.

As the solvent, a mixed solvent of alcohol solvent and a halogen solvent is preferable, and a mixed solvent of ethanol and chloroform is more preferable. The amount of the solvent to be used is generally 10- to 100-fold volume, preferably 10-20 to 50-fold volume, relative to compound A13.

Examples of the reduction catalyst include palladium hydroxide, palladium hydroxide-activated carbon, platinum oxide, Raney-nickel and the like. As the amount of the reduction catalyst to be used, a catalytic amount relative to compound A13 is generally sufficient.

The reaction time is generally 1-24 hr, preferably 12-24 hr. The reaction temperature is generally 0° C.-room temperature, preferably room temperature.

After completion of the reaction, the reaction liquid is filtered, the filtrate is concentrated under reduced pressure, and the residue is purified by column chromatography, whereby desired compound A can be obtained in a good yield.

Scheme 3

A6 →(Step 10)

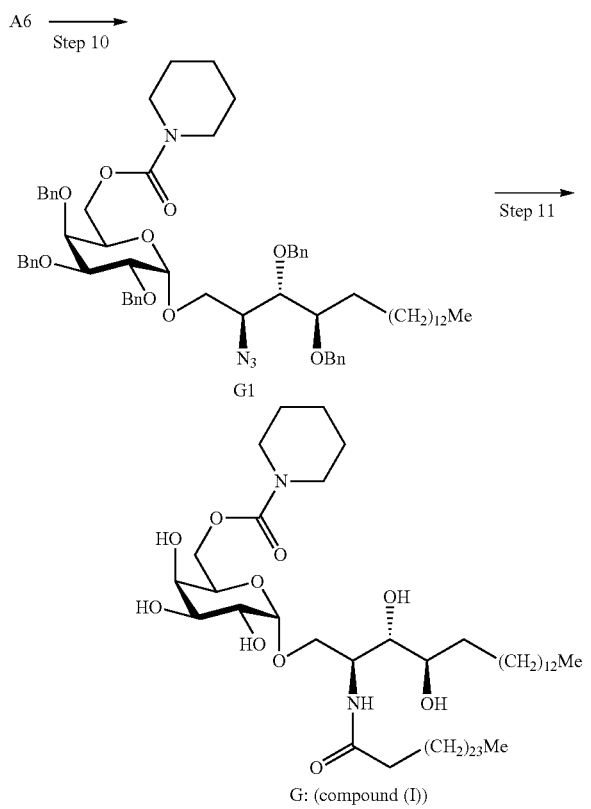

G: (compound (I))

[Step 10]

In Step 10, the 6-position hydroxyl group of compound A6 is carbonylated, and further bonded to piperidine to give compound G1. To be specific, compound A6 is reacted with a carbonylating reagent in a solvent and, after the reaction, reacted with piperidine.

As the carbonylating reagent, phosgene, a dimer or trimer thereof, chlorocarbonate and the like are used.

The solvent is not particularly limited as long as it does not inhibit the reaction. For example, halogen solvents (e.g., methylene chloride, dichloromethane, chloroform) are preferably used.

A base may be added as necessary. Examples of the base include pyridine, triethylamine and the like, and pyridine is preferable.

The amount of the solvent to be used is generally 5- to 100-fold volume, preferably 20- to 50-fold volume, relative to compound A6.

The amount of the base to be used is generally 1-50 equivalents, preferably 2-20 equivalents, relative to compound A6.

The reaction temperature is generally 0-50° C., preferably at room temperature, and the reaction time is generally 30 min-24 hr.

Compound G1 can be isolated by a conventional method. For example, after completion of the reaction, the reaction mixture is concentrated under reduced pressure, and the residue is purified by column chromatography, whereby compound G1 can be isolated.

[Step 11]

In Step 11, compound G1 is converted to compound G. Compound G is encompassed in compound (I).

This step is performed in the same manner as in Steps 7-9 except that the starting compound is compound G1 instead of compound A10.

Scheme 4

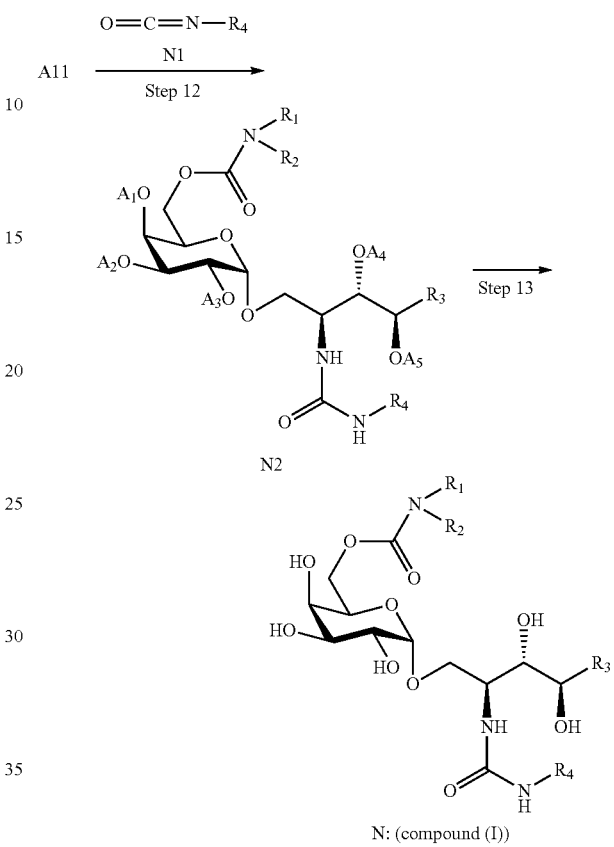

N: (compound (I))

[Step 12]

In Step 12, the amino group of compound A11 is converted to a ureido group to give compound N2. To be specific, compound A11 is reacted with compound N1 in a solvent and, where necessary, in the presence of a base. Compound N1 (starting material compound) can be synthesized by a known method, or is commercially available.

While the solvent is not particularly limited as long as the reaction is not inhibited, for example, halogen solvents (e.g., dichloromethane, chloroform) are preferably used.

Where necessary, a base may be added. Examples of the base include pyridine, triethylamine and the like.

The amount of the solvent to be used is generally 5- to 100-fold volume, preferably 20- to 50-fold volume, relative to compound A11.

The amount of the base to be used is generally 10 to 50 equivalents, preferably 10 to 20 equivalents, relative to compound A11.

The amount of compound N1 to be used is generally 1 to 20 equivalents, preferably 1 to 10 equivalents, relative to compound A11.

The reaction temperature is generally −20° C. to room temperature, and the reaction time is generally 1 to 24 hr.

After completion of the reaction, compound N2 can be isolated and purified by a conventional method. For example, the reaction mixture is diluted with water, and extracted with an ether solvent such as diethyl ether and the like, an ester solvent such as ethyl acetate and the like. When pyridine is used as the base, the obtained organic layer is washed with saturated aqueous copper sulfate solution, washed with water, saturated brine and the like, and dried over anhydrous magnesium sulfate and the like. After filtration, the filtrate is concentrated under reduced pressure, and the residue is purified by column chromatography and the like to give compound N2.

[Step 13]

In Step 13, compound N2 is converted to compound N. Compound N is encompassed in compound (I).

This step is performed in the same manner as in Step 9 except that the starting compound is compound N2 instead of compound A13.

By administering compound (I) or a salt thereof of the present invention (hereinafter to be also referred to as "carbamate glycolipid of the present invention"), NKT cell can be activated, and IFN-γ production can be selectively and preferentially induced. Different from the conventional α-galactosylceramide, moreover, an increase in the IL-4 production is suppressed. Therefore, the prophylaxis or treatment of cancer or infection and the like is possible without aggravating the disease state. The carbamate group of the glycolipid of the present invention is not easily metabolized as compared to amide group. Consequently, NKT cells can be intensely activated for a long time. Furthermore, even with a smaller dose of administration than that of α-galactosylceramide, NKT cells can be potently activated to increase the amount of IFN-γ produced.

By pulsing human dendritic cells with the carbamate glycolipid of the present invention and administering the dendritic cells to a subject, a stronger IFN-γ production inducing action can be obtained. The human dendritic cell used here is not particularly limited as long as it is a human-derived dendritic cell (hDC) capable of activating NKT cells via the carbamate glycolipid of the present invention, and may be any of myeloid dendritic cell (DC1) and lymphoid dendritic cell (DC2), with preference given to DC1. hDC may be prepared by any method known per se, and can also be separated from human epidermis, T cells region of lymphoid tissue, peripheral non-lymphoid tissue, afferent lymph, corium and the like. Preferably, it can be prepared by, for example, separating monocyte, myelocyte and the like from human peripheral blood and the like by a density gradient centrifugation method and the like, and culturing same for about 7-about 10 days in the presence of GM-CSF and IL-4.

hDC can be pulsed with the carbamate glycolipid of the present invention by a well-known conventional method. For example, hDC can be pulsed by being cultivated in a medium (e.g., RPMI-1640 medium etc.) containing the carbamate glycolipid of the present invention at a concentration of about 100-about 200 ng/ml for about 12-about 48 hr. The pulsing may also be performed by adding the glycolipid of the present invention to the medium in the process of culturing and maturing the above-mentioned immature hDC in the presence of GM-CSF and IL-4.

While the presence or absence of activation of NKT cells and the level thereof can be measured by any method known per se. For example, activation of NKT cells can be evaluated by using the amount of cytokine produced by activated NKT cells as an index. As the cytokine produced by activated NKT cells, IFN-γ, IL-4, GM-CSF, IL-10 and the like can be mentioned. The glycolipid of the present invention selectively induces production of IFN-γ.

The production of cytokine in NKT cells can be measured by, for example, using an antibody to the cytokine. For example, activation of NKT cells can also be evaluated by a conventional immunoassay such as ELISA method, RIA method, FIA method, EIA method and the like and by using the cell culture supernatant. In a preferable embodiment, a method including contacting an NKT cell-containing sample with a solid phase immobilized with an anti-cytokine antibody and, after solid-liquid separation, detecting and counting cytokines bond to the solid phase by a sandwich method by using a labeled anti-cytokine antibody. Examples of the label include enzyme, fluorescent substance, luminescence substance, dye, radioisotope and the like. A biotinylated anti-cytokine antibody and label-bound (strept)avidin may also be used. An assay system using enzymes such as alkaline phosphatase and the like as a label is known by the name of ELISPOT for the detection of cytokine-producing cells.

The diseases that can be prevented or treated by the carbamate glycolipid of the present invention are not particularly limited as long as increase of IFN-γ production is expected to show a direct or indirect prophylactic or therapeutic effect thereon. Examples thereof include various carcinomas (e.g., breast cancer, colorectal cancer, lung cancer, prostate cancer, esophagus cancer, gastric cancer, liver cancer, biliary cancer, spleen cancer, kidney cancer, urinary bladder cancer, uterine cancer, testis cancer, thyroid cancer, pancreatic cancer, brain tumor, ovarian cancer, skin cancer, blood tumor (e.g., adult T cell leukemia, chronic myeloid leukemia, malignant lymphoma and the like) and the like); various infections, for example, viral disease (e.g., viral hepatitis due to HEPATITIS B virus, HEPATITIS C virus, HEPATITIS D virus, herpes, acquired immunodeficiency syndrome (AIDS) and the like), bacterial infections (e.g., medicament resistance tuberculosis, atypical mycobacterial infection and the like), mycosis (e.g., candidosis and the like) and the like in mammals (e.g., mouse, cat, bovine, dog, horse, goat, monkey, human).

In addition, as long as the efficacy is not impaired, the carbamate glycolipid of the present invention can be used in combination with other medicaments, for example, existing anti-cancer agents, antiviral drugs, antibacterial drugs, antifungal drugs and the like. In this case, the period for administration is not limited and these agents may be administered to the subject simultaneously or in time intervals. The dose can be appropriately determined by taking into account the clinically adopted dose as a standard. The mixing ratio of the carbamate glycolipid of the present invention to the concomitant drug may be appropriately determined depending on the administration subject, administration route, target disease, conditions, combination, and the like.

Examples of the existing anticancer agents include chemotherapeutic drugs, hormone therapeutic drugs, immunotherapeutic drugs, and the like.

Examples of the chemotherapeutic drugs include alkylating drugs (e.g., Cyclophosphamide, Iphosphamide, Nimustine, Ranimustine, Carboquone, etc.), antimetabolic drugs (e.g., Methotrexate, 5-Fluorouracil, Tegafur, Carmofur, UFT, Doxyfluridine, Cytarabine, Enocitabine, Mercaptopurine, Mercaptopurine riboside, Thioguanine, etc.), anti-cancer antibiotics (e.g., Mytomicin, Adriamycin, Daunorubicin, Epirubicin, Pirarubicin, Idarubicin, Bleomycin, Peplomycin, Actinomycin, etc.), plant-derived anticancer agents (e.g., Vincristine, Vinblastine, Vindesine, Etoposide, Camptothecine, Irinotecan, etc.), Cisplatin, Carboplatin, Nedaplatin, Paclitaxel, Docetaxel, Estramustine, and the like.

Examples of the hormone therapeutic drugs include adrenocortical hormones (e.g., Prednisolone, Prednisone, Dexamethasone, Cortisone acetate, etc.), estrogens (e.g., Estradiol, Ethynylestradiol, Fosfestrol, Clorotrianisene, etc.), antiestrogens (e.g., Epithiostanol, Mepitiostane, Tamoxifen, Clomiphene, etc.), luteinizing hormones (e.g., Hydroxyprogesterone caproate, Dydrogesterone, Medroxyprogesterone, Norethysterone, Norethindrone, etc.), LHRH derivatives (e.g., Leuprorelin acetate, etc.) and the like.

Examples of the immunotherapeutic drugs include microorganism- or bacterium-derived components (e.g., muramyl dipeptide derivatives, Picibanil, etc.), polysaccharides having an immunopotentiating activity (e.g., lentinan, schizophyllan, krestin, etc.), genetically engineered cytokines (e.g., interferons, interleukin 2 (IL-2), interleukin 12 (IL-12), tumor necrosis factor (TNF), etc.), colony stimulating agents (e.g., granulocyte colony stimulating factor, erythropoietin, etc.) and the like.

Examples of the antiviral drug include nucleic acid synthesis inhibitory antiviral drugs (e.g., acyclovir, ganciclovir, vidarabine, foscarnet, zidovudine, lamivudine, didanosine, etc.), intracellular invasion inhibitory antiviral drugs (e.g., amantadine, zanamivir, oseltamivir etc.), host phylaxis ability enhancing antiviral drugs (e.g., interferon, isoprinosine, etc.), and the like.

Examples of the antibacterial drug include penicillin antibiotics (e.g., sawacillin, pasetocin, yamacillin, bacacil, viccillin, pentrex etc.), cephem antibiotics (e.g., keflex, kefral, cefzon, tomiron, cefspan, pansporin etc.), macrolide antibiotics (e.g., erythrosine, clarith, klaricid, rulid, josamycin etc.), tetracycline antibiotics (e.g., minomycin, vibramycin, hydramycin, ledermycin etc.), fosfomycin antibiotics (e.g., fosmicin, eukocin etc.), aminoglycoside antibiotics (e.g., kanamycin, etc.), new quinolone antibacterial drug (e.g., cravit, tarivid, baccidal, tosuxacin, ozex etc.), and the like.

Examples of the antifungal agent include polyene antifungal drugs (e.g., trichomycin, amphotericin B, nystatin, etc.), imidazole antifungal drugs (e.g., econazole, miconazole, clotrimazole, etc), triazole antifungal drugs (e.g., fluconazole, itoraconazole, etc.), allylamine antifungal drugs (e.g., butenafine, terbinafine hydrochloride, etc.), flucytosine (5-FC) antifungal drugs (e.g., flucytosine, etc.), and the like.

When the carbamate glycolipid of the present invention is administered to a human, it can be safely administered orally or parenterally, as is or after being blended with a pharmacologically acceptable carrier, excipient, diluent and the like, in the form of pharmaceutical compositions such as oral preparations (e.g., powders, granules, tablets, capsules), parenteral preparations (e.g., injections), and suppositories (e.g., rectal suppositories, vaginal suppositories). These preparations can be produced by conventionally known methods.

Examples of the injection include subcutaneous injections, intravenous injections, intramuscular injections, intraperitoneal injections, drip infusions and the like. An injection can be prepared as an aqueous injection by treating the glycolipid of the present invention in the presence of a solubilizer (e.g., β-cyclodextrins), a dispersing agent (e.g., carboxymethylcellulose, sodium alginate), a preservative (e.g., methylparaben, propylparaben, benzyl alcohol, chlorobutanol), an isotonizing agent (e.g., sodium chloride, glycerol, sorbitol, glucose) and the like by a conventional method. An injection can also be prepared as an oily injection by dissolving, suspending or emulsifying the glycolipid of the present invention in a vegetable oil (e.g., olive oil, sesame oil, peanut oil, cottonseed oil, corn oil), propylene glycol and the like.

An oral preparation can also be produced by adding to the carbamate glycolipid of the present invention, for example, an excipient (e.g., lactose, saccharose, starch), a disintegrant (e.g., starch, calcium carbonate), a binder (e.g., starch, gum arabic, carboxymethylcellulose, polyvinylpyrrolidone, hydroxypropylcellulose) or a lubricant (e.g., talc, magnesium stearate, polyethyleneglycol) and the like as appropriate, compression molding the mixture, and then, as required, coating the mixture with hydroxypropylmethylcellulose and the like. A suppository can be produced by blending the carbamate glycolipid of the present invention with a non-irritant excipient (e.g., polyethylene glycol, glycerides of higher fatty acids).

The dose of the carbamate glycolipid of the present invention varies depending on the age, body weight, symptoms, dosage form, method of administration, duration of administration and the like; for example, for a patient (adult, weighing about 60 kg), a daily dose of 0.1 to 1 mg/kg, preferably 0.5 to 1 mg/kg, more preferably 0.8 to 1 mg/kg, is administered orally or parenterally in a single to several divided portions.

In an attempt to induce IFN-γ production, it is also possible to pulse dendritic cells with the carbamate glycolipid of the present invention, and administer the dendritic cells to patients. Therefore, the present invention provides a selective IFN-γ production inducer containing dendritic cells pulsed with the carbamate glycolipid of the present invention.

The agent can be produced as an oral/parenteral preparation according to a conventional means, by mixing an effective amount of the above-mentioned hDC pulsed with the carbamate glycolipid of the present invention with a pharmaceutically acceptable carrier, and the like. The agent is generally produced as a parenteral preparation such as injection, suspension, drip infusion and the like. Examples of the pharmaceutically acceptable carrier that can be contained in the parenteral preparation include aqueous solutions for injection such as physiological saline, isotonic solution containing glucose and other auxiliary agents (e.g., D-sorbitol, D-mannitol, sodium chloride and the like) and the like. The agent of the present invention may be blended with, for example, buffering agent (e.g., phosphate buffer, sodium acetate buffer), soothing agent (e.g., benzalkonium chloride, procaine hydrochloride and the like), stabilizer (e.g., human serum albumin, polyethylene glycol and the like), preservative, antioxidant and the like. When the agent is formulated as an aqueous suspension, hDCs pulsed with the carbamate glycolipid of the present invention only needs to be suspended in the above-mentioned aqueous solution at about $5\times10^6$-about $1\times10^7$ cells/ml. Since the thus-obtained preparation is stable and of lower toxicity, it can be safely administered to human. While the subject of administration is preferably the patient him/herself the hDC derives from (i.e., autologous transplantation), the subject is not limited when it is a human predicted to have compatibility with the hDC to be administered. The administration method is not particularly limited, and oral or parenteral administration can be employed. Preferred is injection or drip administration, and intravenous administration, subcutaneous administration, intradermal administration, intramuscular administration, intraperitoneal administration, direct administration to the affected part and the like can be mentioned. While the dose of the agent of the present invention varies depending on the subject of administration, target organ, symptom, administration method and the like, a single dose thereof is generally about $6 \times 10^5$-about $1 \times 10^7$ cells in the amount of hDC, which is, for example, conveniently administered parenterally to an adult patient (body weight 60 kg) about 4-about 8 times at about 1-about 2 weeks intervals.

EXAMPLES

The present invention is explained in more detail in the following by referring to Examples and Experimental Examples, which are not to be construed as limitative.

Example 1

Synthesis and Purification Method of RCAI-123 (Encompassed in Compound A)

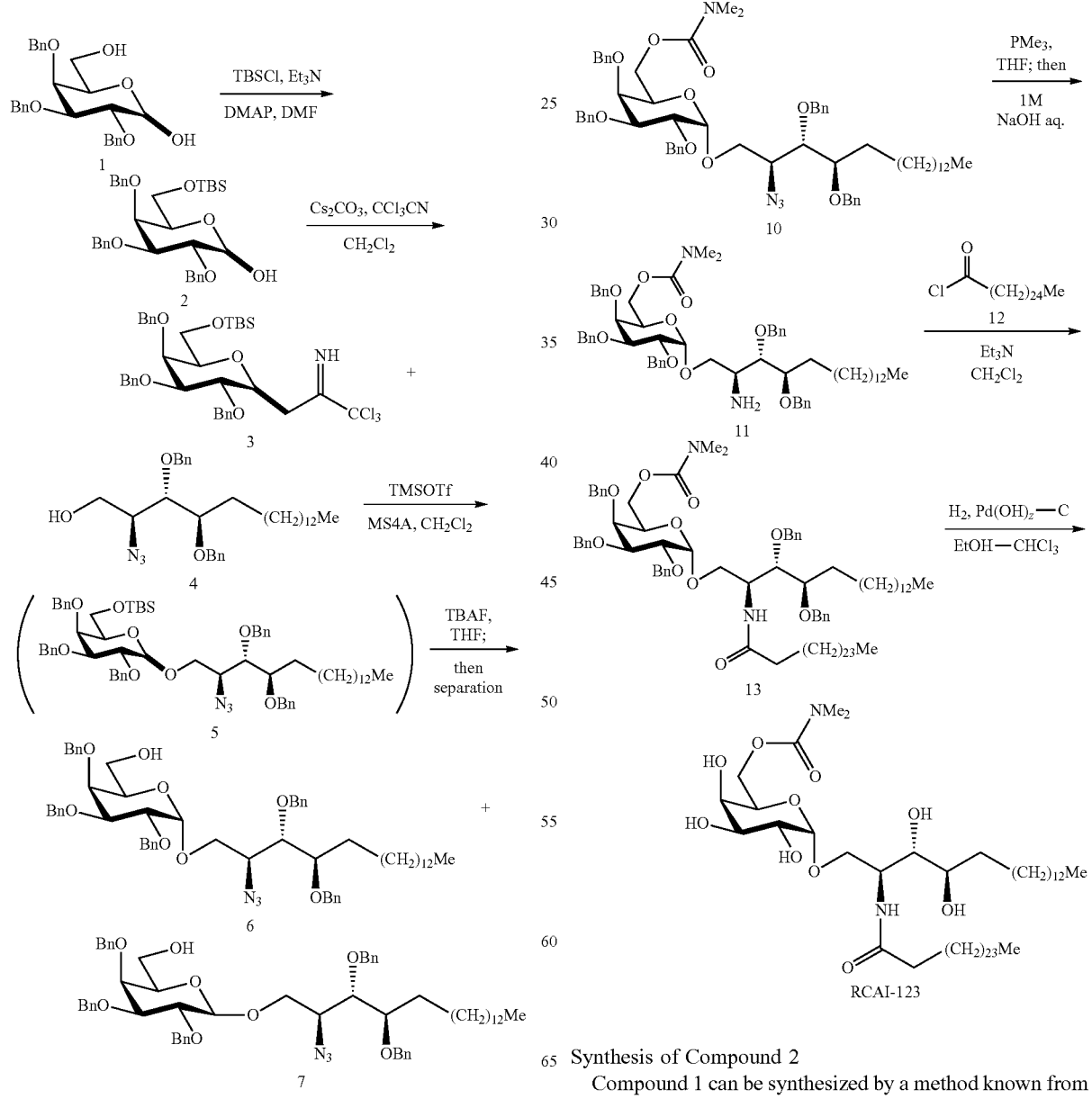

Synthesis of Compound 2

Compound 1 can be synthesized by a method known from document (Carbohydr. Res., 1979, 73, 273). To a solution of compound 1 (6.03 g, 13.4 mmol) and triethylamine (9.3 mL, 67 mmol) in N,N-dimethylformamide (120 mL) were added tert-butyldimethylsilyl chloride (2.21 g, 14.7 mmol) and 4-(N,N-dimethylamino)pyridine (163 mg, 1.33 mmol) at 0° C. The To reaction mixture was stirred at room temperature for 15 hr, water was added, and the mixture was extracted with ethyl acetate. The organic layer was successively washed with water and saturated brine, and dried over anhydrous magnesium sulfate. After filtration, the filtrate was concentrated under reduced pressure and the solvent was evaporated. The residue was purified by silica gel column chromatography (80 g, hexane:ethyl acetate=10:1) to give compound 2 (7.04 g, 93%, mixture of α-form:β-form=about 3:2) as a colorless oil.

IR (film): $\nu_{max}$=3420 (br m, OH), 1610 (w), 1585 (w), 1495 (m), 1255 (m, t-Bu, Si-Me), 1100 (br s, C—O), 840 (br s), 735 (br s), 700 (s) cm$^{-1}$.

$^1$H-NMR (500 MHz, CDCl$_3$): δ=7.38-7.19 (15H, m), 5.26 (0.6H, dd, J=4.0, 2.0 Hz, α-1-H), 4.65 (0.4H, t, J=7.0 Hz, β-1-H), 2.94 (0.4H, d, J=7.0 Hz, β-OH), 2.86 (0.6H, d, J=2.0 Hz, α-OH), 0.88 (9H, s, t-Bu), 0.04 (3H, s, SiMe), 0.03 (3H, s, SiMe) ppm.

HR-ESIMS: Calcd for [M+Na]$^+$ (C$_{33}$H$_{44}$O$_6$SiNa): 587.2799. Found: 587.2799.

Synthesis of Compound 3

To a solution of compound 2 (2.02 g, 3.58 mmol) in dichloromethane (50 mL) were added trichloroacetonitrile (3.65 mL, 36.1 mmol) and cesium carbonate (590 mg, 1.81 mmol) at room temperature. The reaction mixture was stirred at room temperature for 16 hr, water was added, and the mixture was extracted with dichloromethane. The organic layer was washed with saturated aqueous sodium hydrogen carbonate solution, and dried over anhydrous potassium carbonate. After filtration, the filtrate was concentrated under reduced pressure, and the solvent was evaporated to give the object compound 3 (2.6 g, mixture of α-form:β-form=about 2:1) as an orange oil. This compound was used for the next operation without further purification.

IR (film): $\nu_{max}$=3340 (w, NH), 1730 (m, C=O), 1670 (s, C=N), 1605 (w), 1590 (w), 1500 (m), 1255 (m, t-Bu, Si-Me), 1105 (br s, C—O), 1060 (br s, C—O), 840 (s), 735 (s), 700 (s) cm$^{-1}$.

$^1$H-NMR (500 MHz, CDCl$_3$): δ=8.61 (0.33H, s, β-NH), 8.51 (0.67H, s, α-NH), 7.38-7.25 (15H, m), 6.51 (0.67H, d, J=3.5 Hz, α-1-H), 5.75 (0.33H, d, J=8.0 Hz, β-1-H), 0.87 (3H, s, β-t-Bu), 0.86 (6H, s, α-t-Bu), 0.04 (1H, s, β-SiMe), 0.03 (1H, s, β-SiMe), 0.01 (2H, s, α-SiMe), 0.00 (2H, s, α-SiMe) ppm.

Synthesis of Compound 5

Compound 4 can be synthesized by a method known from document (Eur. J. Org. Chem., 1998, 291). To a suspension of compound 4 (1.51 g, 2.88 mmol), compound 3 (2.6 g) obtained by the above-mentioned process and molecular sieves (4A, powder, 9.3 g) in anhydrous dichloromethane (50 mL) was added trimethylsilyl trifluoromethanesulfonate (26 μL, 0.14 mmol) at 40° C. (oil bath temperature). The reaction mixture was stirred at 40° C. (oil bath temperature) for 15 min, cooled to room temperature and filtered. After filtration, the filtrate was washed with saturated aqueous sodium hydrogen carbonate solution, and the organic layer was dried over anhydrous potassium carbonate. After filtration, the filtrate was concentrated under reduced pressure and the solvent was evaporated. The residue was purified by silica gel column chromatography (50 g, hexane:ethyl acetate=20:1) to give compound 5 (2.69 g, 87%, mixture of α-form:β-form=about 3:1) as a colorless oil.

IR (film): $\nu_{max}$=2100 (s, N$_3$), 1605 (w), 1585 (w), 1495 (m), 1255 (m, t-Bu, Si-Me), 1105 (br s, C—O), 1060 (br s, C—O), 840 (br s), 735 (s), 700 (s) cm$^{-1}$.

$^1$H-NMR (500 MHz, CDCl$_3$): δ=4.89 (0.75H, d, J=3.5 Hz, α-1'-H), 4.34 (0.25H, d, J=7.5 Hz, 0.88 (3H, t, J=6.5 Hz, 18-H$_3$), 0.87 (2.25H, s, β-t-Bu), 0.86 (6.75H, s, α-t-Bu), 0.019 (0.75H, s, β-SiMe), 0.016 (0.75H, s, β-SiMe), 0.009 (2.25H, s, α-SiMe), 0.002 (2.25H, s, α-SiMe) ppm.

HR-ESIMS: Calcd for [M+Na]$^+$ (C$_{65}$H$_{91}$N$_3$O$_8$SiNa): 1092.6468. found: 1092.6464.

Synthesis of Compounds 6, 7

To a solution of compound 5 (2.69 g, 2.51 mmol, mixture of α-form:β-form=about 3:1) obtained by the above-mentioned process in tetrahydrofuran (50 mL) was added a solution (1.0M, 5.0 mL, 5.0 mmol) of tetrabutylammonium fluoride in tetrahydrofuran at room temperature. The reaction mixture was stirred at room temperature for 3 hr, water was added, and the mixture was extracted with ethyl acetate. The organic layer was successively washed with water and saturated brine, and dried over anhydrous magnesium sulfate. After filtration, the filtrate was concentrated under reduced pressure, and the solvent was evaporated. The residue was purified by silica gel column chromatography (30 g) to give compound 6 (α-form, hexane:ethyl acetate=5:1, 1.67 g, 70%) and compound 7 (β-form, hexane:ethyl acetate=3:1, 612 mg, 25%) each as a colorless oil. α-form: $n_D^{24}$=1.5171.

$[α]_D^{25}$=+24.8 (c=1.00, CHCl$_3$).

IR (film): $\nu_{max}$=3480 (br m, OH), 2100 (s, N$_3$), 1605 (w), 1585 (w), 1500 (m), 1100 (br s, C—O), 1060 (br s, C—O), 735 (br s), 700 (s) cm$^{-1}$.

$^1$H-NMR (500 MHz, CDCl$_3$): δ=7.41-7.20 (25H, m), 4.96 (1H, d, J=12 Hz), 4.91 (1H, d, J=3.0 Hz), 4.87 (1H, d, J=12 Hz), 4.81 (1H, d, J=12 Hz), 4.75 (1H, d, J=12 Hz), 4.70 (1H, d, J=12 Hz), 4.66 (1H, d, J=12 Hz), 4.63 (1H, d, J=12 Hz), 4.61 (1H, d, J=12 Hz), 4.57 (1H, d, J=12 Hz), 4.50 (1H, d, J=12 Hz), 4.66 (1H, dd, J=10, 3.5 Hz), 3.99-3.95 (2H, m), 3.85 (1H, br s), 3.75-3.68 (4H, m), 3.63 (1H, dd, J=12, 3.5 Hz), 3.64-3.60 (1H, m), 3.40 (1H, ddd, J=12, 8.5, 5.0 Hz), 1.69-1.60 (2H, m), 1.57-1.50 (2H, m), 1.44-1.34 (1H, m), 1.34-1.21 (22H, m), 0.88 (3H, t, J=7.0 Hz) ppm.

HR-ESIMS: Calcd for [m+Na]$^+$ (C$_{59}$H$_{77}$N$_3$O$_8$Na): 978.5603. found: 978.5601.

β-form:

$n_D^{24}$=1.5177.

$[α]_D^{25}$=−0.48 (c=1.02, CHCl$_3$).

IR (film): $\nu_{max}$=3460 (br m, OH), 2100 (s, N$_3$), 1605 (w), 1585 (w), 1495 (m), 1090 (br s, C—O), 735 (br s), 700 (s) cm$^{-1}$.

$^1$H-NMR (500 MHz, CDCl$_3$): δ=7.47-7.21 (25H, m), 4.96 (1H, d, J=12 Hz), 4.94 (1H, d, J=12 Hz), 4.81 (1H, d, J=12 Hz), 4.79 (1H, d, J=12 Hz), 4.74 (1H, d, J=12 Hz), 4.68 (1H, d, J=12 Hz), 4.65 (1H, d, J=12 Hz), 4.64 (1H, d, J=12 Hz), 4.57 (1H, d, J=12 Hz), 4.51 (1H, d, J=12 Hz), 4.34 (1H, J=8.0 Hz), 4.12 (1H, dd, J=10, 7.5 Hz), 3.89-3.84 (2H, m), 3.77 (1H, dd, J=10, 3.0 Hz), 3.78-3.75 (1H, m), 3.72-3.65 (2H, m), 3.62 (1H, br quint., J=4.0 Hz), 3.51 (1H, dd, J=10, 3.0 Hz), 3.45 (1H, ddd, J=11, 8.5, 4.0 Hz), 3.30 (1H, br t, J=6.5 Hz), 1.71-1.63 (1H, m), 1.58-1.50 (2H, m), 1.44-1.34 (2H, m), 1.33-1.22 (22H, m), 0.88 (3H, t, J=7.0 Hz) ppm.

HR-ESIMS: Calcd for [M+Na]$^+$ (C$_{59}$H$_{77}$N$_3$O$_8$Na): 978.5603. found: 978.5595.

Synthesis of Compound 9

Compound 8 can be synthesized by a method known from document (Synthesis, 1993, 103). To a solution of compound 6 (1.05 g, 1.10 mmol) and pyridine (444 μL, 5.49 mmol) in tetrahydrofuran-N,N-dimethylformamide (1:1, 40 mL) was added compound 8 (589 mg, 3.32 mmol) at 0° C. The reaction mixture was stirred at room temperature for 16 hr, water was added, and the mixture was extracted with ethyl acetate. The organic layer was successively washed with water, saturated aqueous copper sulfate solution, water, saturated aqueous sodium hydrogen carbonate solution and saturated brine, and dried over anhydrous magnesium sulfate. After filtration, the filtrate was concentrated under reduced pressure, and the solvent was evaporated. The residue was purified by silica gel column chromatography (30 g, hexane:ethyl acetate=5:1) to give compound 9 (1.23 g, quant.) as a colorless oil.

$n_D^{22}$=1.5171.

$[\alpha]_D^{22}$=+26.4 (c=1.03, CHCl$_3$).

IR (film): $\nu_{max}$=2100 (s, N$_3$), 1815 (s, C=O), 1790 (s, C=O), 1750 (br s, C=O), 1605 (w), 1585 (w), 1495 (m), 1230 (br s), 1100 (br s, C—O), 740 (br s), 700 (s) cm$^{-1}$.

$^1$H-NMR (500 MHz, CDCl$_3$): δ=7.40-7.22 (25H, m), 4.97 (1H, d, J=12 Hz), 4.90 (1H, d, J=3.5 Hz), 4.88 (1H, d, J=12 Hz), 4.78 (1H, d, J=12 Hz), 4.76 (1H, d, J=12 Hz), 4.68 (1H, d, J=12 Hz), 4.66 (1H, d, J=12 Hz), 4.63 (1H, d, J=12 Hz), 4.58 (1H, d, J=12 Hz), 4.57 (1H, d, J=12 Hz), 4.52 (1H, d, J=12 Hz), 4.32 (1H, dd, J=11, 7.5 Hz), 4.04 (1H, dd, J=10, 3.0 Hz), 4.01 (1H, dd, J=11, 5.0 Hz), 4.01-3.96 (2H, m), 3.94-3.91 (1H, m), 3.83-3.81 (1H, m), 3.78-3.69 (3H, m), 3.63-3.60 (1H, m), 2.76 (4H, s), 1.70-1.62 (1H, m), 1.59-1.51 (1H, m), 1.44-1.35 (1H, m), 1.35-1.20 (23H, m), 0.88 (3H, t, J=7.0 Hz) ppm.

HR-ESIMS: Calcd for [M+Na]$^+$ (C$_{64}$H$_{80}$N$_4$O$_{12}$Na): 1119.5670. found: 1119.5671.

Synthesis of Compound 10

To a solution of compound 9 (122 mg, 0.111 mmol) and diisopropylethylamine (97 μL, 0.557 mmol) in N,N-dimethylformamide (5 mL) was added dimethylamine hydrochloride (18 mg, 0.221 mmol) at room temperature. The reaction mixture was stirred at room temperature for 17 hr, water was added, and the mixture was extracted with ethyl acetate. The organic layer was successively washed with water, saturated aqueous sodium hydrogen carbonate solution and saturated brine, and dried over anhydrous magnesium sulfate. After filtration, the filtrate was concentrated under reduced pressure, and the solvent was evaporated. The residue was purified by silica gel column chromatography (30 g, hexane:ethyl acetate=5:1) to give compound 10 (101 mg, 89%) as a colorless oil.

$n_D^{24}$=1.5178.

$[\alpha]_D^{26}$=+24.6 (c=1.04, CHCl$_3$).

IR (film): $\nu_{max}$=2300 (s, N$_3$), 1710 (s, C=O), 1605 (w), 1500 (m), 1100 (br s, C—O), 1060 (br s, C—O), 735 (br s), 700 (s) cm$^{-1}$.

$^1$H-NMR (500 MHz, CDCl$_3$): δ=7.40-7.19 (25H, m), 4.96 (1H, d, J=12 Hz), 4.91 (1H, d, J=4.0 Hz), 4.87 (1H, d, J=12 Hz), 4.79 (1H, d, J=12 Hz), 4.74 (1H, d, J=12 Hz), 4.68 (1H, d, J=12 Hz), 4.66 (1H, d, J=12 Hz), 4.62 (1H, d, J=12 Hz), 4.60 (1H, d, J=12 Hz), 4.57 (1H, d, J=12 Hz), 4.49 (1H, d, J=12 Hz), 4.13 (1H, dd, J=11, 7.0 Hz), 4.09-4.06 (2H, m), 3.99 (1H, dd, J=10, 3.0 Hz), 3.97 (1H, dd, J=10, 2.0 Hz), 3.93 (1H, br t, J=7.0 Hz), 3.86-3.85 (1H, m), 3.74 (1H, dd, J=6.5, 4.5 Hz), 3.70 (1H, dd, J=10, 6.5 Hz), 3.69-3.65 (1H, m), 3.61 (1H, quint.-like, J=4.0 Hz), 2.84 (3H, s), 2.70 (3H, s), 1.70-1.62 (1H, m), 1.57-1.50 (2H, m), 1.44-1.35 (1H, m), 1.33-1.20 (22H, m), 0.88 (3H, t, J=7.0 Hz) ppm.

HR-ESIMS: Calcd for [M+Na]$^+$ (C$_{62}$H$_{82}$N$_4$O$_9$Na): 1049.5980. found: 1049.5964.

Synthesis of Compound 11

To a solution of compound 10 (217 mg, 0.211 mmol) in dry tetrahydrofuran (10 mL) was added a solution (1.0 M, 1.1 mL, 1.1 mmol) of trimethylphosphine in tetrahydrofuran at 0° C. The reaction mixture was stirred at room temperature for 15 hr, and m aqueous sodium hydroxide solution (1.0 M, 2.2 mL, 2.2 mmol) was added. After stirring further at room temperature for 6 hr, water was added, and the mixture was extracted with ethyl acetate. The organic layer was successively washed with water, saturated aqueous sodium hydrogen carbonate solution, and dried over anhydrous potassium carbonate. After filtration, the filtrate was concentrated under reduced pressure, and the solvent was evaporated. The residue was purified by silica gel column chromatography (NH silica, 30 g, hexane:ethyl acetate=1:1) to give compound 11 (161 mg, 76%) as a colorless oil.

$n_D^{24}$=1.5173.

$[\alpha]_D^{24}$=+24.3 (c=1.02, CHCl$_3$).

IR (film): $\nu_{max}$=3380 (w, NH), 1710 (br s, C=O), 1600 (w), 1500 (m), 1140 (br s, C—O), 1100 (br s, C—O), 1060 (br s, C—O), 735 (br s), 695 (s) cm$^{-1}$.

$^1$H-NMR (500 MHz, CDCl$_3$): δ=7.40-7.23 (25H, m), 4.96 (1H, d, J=12 Hz), 4.90 (1H, d, J=3.5 Hz), 4.86 (1H, d, J=12 Hz), 4.78 (1H, d, J=12 Hz), 4.75 (1H, d, J=12 Hz), 4.70 (1H, d, J=12 Hz), 4.66 (1H, d, J=12 Hz), 4.63 (1H, d, J=12 Hz). 4.61 (1H, d, J=12 Hz), 4.54 (1H, d, J=12 Hz), 4.50 (1H, d, J=12 Hz), 4.14-4.07 (2H, m), 4.07 (1H, dd, J=10, 4.0 Hz), 3.96-3.92 (3H, m), 3.87 (1H, br s), 3.72-3.69 (1H, m), 3.55-3.52 (1H, m), 3.39 (1H, br t, J=9.0 Hz), 3.19-3.15 (1H, m), 2.83 (3H, s), 2.68 (3H, s), 1.72-1.62 (1H, m), 1.62-1.51 (2H, m), 1.51-1.42 (1H, m), 1.34-1.20 (22H, m), 0.88 (3H, t, J=7.0 Hz) ppm.

HR-ESIMS: Calcd for [M+H]$^+$ (C$_{62}$H$_{85}$N$_2$O$_9$): 1001.6255. found: 1001.6241.

Synthesis of Compound 13

Compound 12 can be synthesized by a method known from document (Org. Lett., 2006, 8, 3375). To a solution of compound 11 (151 mg, 0.151 mmol) and triethylamine (105 μL, 0.757 mmol) in anhydrous dichloromethane (10 mL) was added a solution of compound 12 (70 mg, 0.17 mmol) in anhydrous dichloromethane (2 mL) at 0° C. The reaction mixture was stirred at room temperature for 18 hr, water was added, and the mixture was extracted with ethyl acetate. The organic layer was successively washed with water, saturated aqueous sodium hydrogen carbonate solution and saturated brine, and dried over anhydrous magnesium sulfate. After filtration, the filtrate was concentrated under reduced pressure, and the solvent was evaporated. The residue was purified by silica gel column chromatography (30 g, hexane:ethyl acetate=4:1) to give compound 13 (183 mg, 88%) as a colorless solid.

$[\alpha]_D^{24}$=+18.4 (c=1.08, CHCl$_3$).

$^1$H-NMR (500 MHz, CDCl$_3$): δ=7.40-7.21 (25H, m), 5.98 (1H, d, J=8.5 Hz), 4.96 (1H, d, J=12 Hz), 4.90 (1H, d, J=4.0 Hz), 4.83 (1H, d, J=12 Hz), 4.79 (1H, d, J=12 Hz), 4.78 (1H, d, J=12 Hz), 4.76 (1H, d, J=12 Hz), 4.64 (2H, d, J=12 Hz), 4.58 (1H, d, J=12 Hz), 4.51 (1H, d, J=12 Hz), 4.45 (1H, d, J=12 Hz), 4.20-4.15 (1H, m), 4.11 (2H, d, J=6.5 Hz), 4.07 (1H, dd, J=10, 4.0 Hz), 3.93-3.85 (4H, m), 3.84 (1H, dd, J=7.5, 2.5 Hz), 3.74 (1H, dd, J=11, 4.0 Hz), 3.49 (1H, dt, J=8.5, 2.5 Hz), 2.83 (3H, s), 2.73 (3H, s), 1.99 (1H, quint., J=7.5 Hz), 1.92 (1H, quint., J=7.5 Hz), 1.69-1.40 (6H, m), 1.40-1.18 (66H, m), 0.88 (6H, t, J=7.0 Hz) ppm.

HR-ESIMS: Calcd for [M+Na]$^+$ (C$_{88}$H$_{134}$N$_2$O$_{10}$Na): 1401.9936. found: 1401.9930.

Synthesis of RCAI-123

To a solution of compound 13 (179 mg, 0.130 mmol) in ethanol-chloroform (4:1, 10 mL) was added palladium hydroxide-activated carbon (20%, wet, 44 mg) at room temperature. Under a hydrogen atmosphere, the mixture was stirred at room temperature for 15 hr, and diluted with a mixed solvent of chloroform-methanol (5:1). After filtration, the filtrate was concentrated under reduced pressure, and the solvent was evaporated. The residue was purified by silica gel column chromatography (6 g, chloroform:methanol=25:2) to give RCAI-123 (101 mg, 84%) as a colorless powder.

Mp 130-132° C.

$[\alpha]_D^{26}$=+49.8 (c=0.30, pyridine).

IR (KBr): $\nu_{max}$=3420 (br s, OH), 3280 (w, NH), 1690 (br s, C=O), 1640 (s, C=O), 1545 (br m), 1210 (br m), 1150 (br m, C—O), 1080 (br s, C—O), 720 (m) cm$^{-1}$.

$^1$H-NMR (500 MHz, pyridine-d$_5$): δ=8.47 (1H, d, J=8.5 Hz), 5.50 (1H, d, J=4.0 Hz), 5.27-5.22 (1H, m), 4.82 (1H, dd, J=11, 7.0 Hz), 4.74 (1H, dd, J=11, 5.0 Hz), 4.64 (1H, dd, J=11, 5.0 Hz), 4.59 (1H, dd, J=9.5, 4.0 Hz), 4.46 (1H, dd, J=7.0, 6.0 Hz), 4.37-4.26 (5H, m), 2.82 (3H, s), 2.81 (3H, s), 2.31-2.24 (1H, m), 1.96-1.85 (2H, m), 1.84-1.78 (2H, m), 1.72-1.63 (1H, m), 1.47-1.16 (66H, m), 0.85 (6H, t, J=7.0 Hz) ppm.

HR-ESIMS: Calcd for [M+Na]$^+$ (C$_{53}$H$_{104}$N$_2$O$_{10}$Na): 951.7589. found: 951.7597.

Example 2

Synthesis and Purification Method of RCAI-124 (Compound B)

By a method similar to that in Example 1, RCAI-124 was synthesized and purified.

The physical properties of RCAI-124 are shown below.

Mp 146-147° C.

$[\alpha]_D^{27}$=+44.2 (c=0.32, pyridine).

IR (KBr): $\nu_{max}$=3340 (br s, OH, NH), 1700 (br s, C=O), 1640 (s, C=O), 1550 (br s), 1275 (br s), 1160 (br m, C—O), 1070 (br s, C—O), 720 (m) cm$^{-1}$.

$^1$H-NMR (500 MHz, pyridine-d$_5$): δ=8.51 (1H, d, J=9.0 Hz), 7.75 (1H, q, J=4.0 Hz), 5.49 (1H, d, J=4.0 Hz), 5.22-5.17 (1H, m), 4.91 (1H, dd, J=11, 7.5 Hz), 4.78 (1H, dd, J=11, 4.5 Hz), 4.62 (1H, dd, J=11, 4.5 Hz), 4.59 (1H, dd, J=9.5, 4.0 Hz), 4.54 (1H, dd, J=7.5, 4.5 Hz), 4.40-4.29 (4H, m), 4.26 (1H, br t, J=9.0 Hz), 2.87 (3H, d, J=4.0 Hz), 2.48-2.38 (2H, m), 2.31-2.22 (1H, m), 1.96-1.84 (2H, m), 1.84-1.74 (2H, m), 1.72-1.62 (1H, m), 1.46-1.16 (66H, m), 0.85 (3H, t, J=7.0 Hz), 0.84 (3H, t, J=7.0 Hz) ppm.

HR-ESIMS: Calcd for [M+Na]$^+$ (C$_{52}$H$_{102}$N$_2$O$_{10}$Na): 937.7432. found: 937.7422.

Example 3

Synthesis and Purification Method of RCAI-137 (Compound C)

By a method similar to that in Example 1, RCAI-137 was synthesized and purified.

The physical properties of RCAI-137 are shown below.

Mp 177-179° C.

$[\alpha]_D^{27}$=+43.1 (c=0.33, pyridine).

IR (KBr): $\nu_{max}$=3340 (br s, OH, NH), 1730 (br s, C=O), 1640 (br s, C=O), 1540 (br m), 1280 (br m), 1130 (br s, C—O), 1080 (br s, C—O), 1040 (br s, C—O), 720 (m) cm$^{-1}$.

$^1$H-NMR (500 MHz, pyridine-d$_5$): δ=11.26 (1H, br s), 11.05 (1H, s), 8.55 (1H, d, J=8.5 Hz), 5.46 (1H, d, J=3.5 Hz), 5.20-5.15 (1H, m), 5.00 (1H, dd, J=11, 7.5 Hz), 4.85 (1H, dd, J=11, 4.5 Hz), 4.62 (1H, dd, J=11, 4.5 Hz), 4.59 (1H, dd, J=10, 4.5 Hz), 4.59-4.44 (1H, m), 4.36-4.25 (5H, m), 2.51-2.39 (2H, m), 2.28-2.21 (1H, m), 1.96-1.84 (2H, m), 1.84-1.74 (2H, m), 1.72-1.63 (1H, m), 1.46-1.16 (66H, m), 0.85 (3H, t, J=7.0 Hz), 0.84 (3H, t, J=7.0 Hz) ppm.

HR-ESIMS: Calcd for [M+Na]$^+$ (C$_{51}$H$_{100}$N$_2$O$_{11}$Na): 939.7225. found: 939.7247.

Example 4

Synthesis and Purification Method of RCAI-138 (Compound D)

By a method similar to that in Example 1, RCAI-138 was synthesized and purified.

The physical properties of RCAI-138 are shown below.

Mp 140-142° C.

$[\alpha]_D^{27}$=+45.2 (c=0.31, pyridine).

IR (KBr): $\nu_{max}$=3320 (br s, OH, NH), 1730 (br s, C=O), 1645 (br s, C=O), 1630 (s, C=O), 1545 (m), 1270 (br m), 1130 (br m, C—O), 1070 (br s, C—O), 720 (m) cm$^{-1}$.

$^1$H-NMR (500 MHz, pyridine-d$_5$): δ=11.69 (1H, s), 8.51 (1H, d, J=8.5 Hz), 5.50 (1H, d, J=3.5 Hz), 5.24-5.19 (1H, m), 4.97 (1H, dd, J=11, 8.0 Hz), 4.81 (1H, dd, J=11, 4.5 Hz), 4.63 (1H, dd, J=10, 4.5 Hz), 4.59 (1H, dd, J=10, 4.0 Hz), 4.53 (1H, dd, J=7.0, 4.5 Hz), 4.34-4.25 (5H, m), 3.85 (3H, s), 2.42 (2H, dt, J=7.5, 3.0 Hz), 2.30-2.23 (1H, m), 1.96-1.84 (2H, m), 1.84-1.75 (2H, m), 1.71-1.62 (1H, m), 1.47-1.16 (66H, m), 0.846 (3H, t, J=7.0 Hz), 0.845 (3H, t, J=7.0 Hz) ppm.

HR-ESIMS: Calcd for [M+Na]$^+$ (C$_{52}$H$_{102}$N$_2$O$_{11}$Na): 953.7381. found: 953.7346.

Example 5

Synthesis and Purification Method of RCAI-148 (Compound E)

By a method similar to that in Example 1, RCAI-148 was synthesized and purified.

The physical properties of RCAI-148 are shown below.

Mp 138-140° C.

$[\alpha]_D^{27}$=+42.8 (c=0.30, pyridine).

IR (KBr): $\nu_{max}$=3340 (br s, OH, NH), 1700 (br s, C=O), 1640 (br s, C=O), 1545 (br s), 1270 (br m), 1140 (br m, C—O), 1080 (br s, C—O), 1040 (br s, C—O), 720 (w) cm$^{-1}$.

$^1$H-NMR (500 MHz, pyridine-d$_5$): δ=8.46 (1H, d, J=8.5 Hz), 7.78 (1H, t, J=5.0 Hz), 5.48 (1H, d, J=3.5 Hz), 5.19-5.14 (1H, m), 4.90 (1H, dd, J=11, 7.5 Hz), 4.77 (1H, dd, J=11, 5.0 Hz), 4.61 (1H, dd, J=11, 5.0 Hz), 4.58 (1H, dd, J=10, 3.5 Hz), 4.54 (1H, dd, J=7.5, 5.0 Hz), 4.37-4.29 (4H, m), 4.25 (1H, br t, J=8.5 Hz), 3.38-3.32 (2H, m), 2.46-2.38 (2H, m), 2.28-2.20 (1H, m), 1.95-1.84 (2H, m), 1.84-1.76 (2H, m), 1.72-1.61 (1H, m), 1.48-1.16 (66H, m), 1.14 (3H, t, J=7.0 Hz), 0.849 (3H, t, J=7.0 Hz), 0.846 (3H, t, J=7.0 Hz) ppm.

HR-ESIMS: Calcd for [M+Na]$^+$ (C$_{53}$H$_{104}$N$_2$O$_{10}$Na): 951.7589. found: 951.7573.

Example 6

Synthesis and Purification Method of RCAI-149 (Compound F)

By a method similar to that in Example 1, RCAI-149 was synthesized and purified.

The physical properties of RCAI-149 are shown below.

Mp 151-153° C.

$[\alpha]_D^{27}$=+45.2 (c=0.31, pyridine).

IR (KBr): $\nu_{max}$=3310 (br s, OH, NH), 1680 (br s, C=O), 1645 (br s, C=O), 1540 (br m), 1285 (m), 1140 (m, C—O), 1080 (br s, C—O), 1045 (br m, C—O), 720 (w) cm$^{-1}$.

$^1$H-NMR (500 MHz, pyridine-$d_5$): δ=8.45 (1H, d, J=9.0 Hz), 5.53 (1H, d, J=3.5 Hz), 5.28-5.23 (1H, m), 4.84 (1H, dd, J=11, 7.5 Hz), 4.77 (1H, dd, J=11, 5.0 Hz), 4.64 (1H, dd, J=11, 5.5 Hz), 4.59 (1H, dd, J=9.5, 4.0 Hz), 4.50 (1H, dd, J=7.5, 5.5 Hz), 4.37-4.28 (4H, m), 4.35 (1H, dd, J=7.5, 4.0 Hz), 3.34-3.20 (4H, m), 2.49-2.39 (2H, m), 2.32-2.25 (1H, m), 1.96-1.86 (2H, m), 1.82 (2H, dquint., J=7.5, 2.5 Hz), 1.72-1.64 (1H, m), 1.48-1.16 (66H, m), 1.07 (4H, br s), 0.850 (3H, t, J=7.0 Hz), 0.848 (3H, t, J=7.0 Hz) ppm.

HR-ESIMS: Calcd for [M+Na]$^+$ ($C_{55}H_{108}N_2O_{10}Na$): 979.7902. found: 979.7913.

Example 7

Synthesis and Purification Method of RCAI-121 (Encompassed in Compound G)

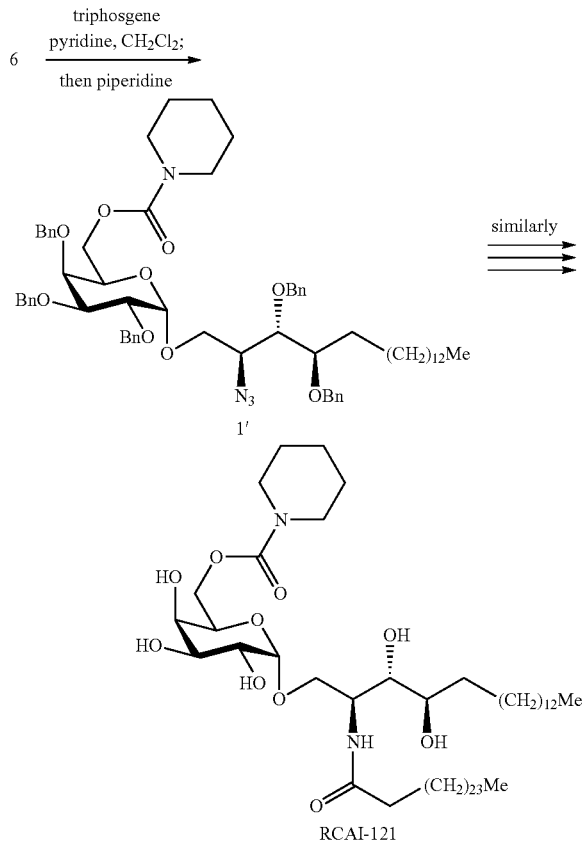

RCAI-121

Synthesis of Compound 1'

To a solution of compound 6 (250 mg, 0.261 mmol) obtained by the above-mentioned process and pyridine (106 μL, 1.31 mmol) in anhydrous dichloromethane (10 mL) was added triphosgene (52 mg, 0.175 mmol) at 0° C. The reaction mixture was stirred at room temperature for 1 hr, and piperidine (129 μL, 1.30 mmol) was added. After stirring further at room temperature for 15 hr, water was added, and the mixture was extracted with ethyl acetate. The organic layer was successively washed with water, 1M hydrochloric acid, water, saturated aqueous sodium hydrogen carbonate solution and saturated brine, and dried over anhydrous magnesium sulfate. After filtration, the filtrate was concentrated under reduced pressure, and the solvent was evaporated. The residue was purified by silica gel column chromatography (30 g, hexane:ethyl acetate=6:1) to give compound 1' (267 mg, 96%) as a colorless oil.

$n_D^{24}$=1.5173.

$[α]_D^{24}$=+25.6 (c=1.02, CHCl$_3$).

IR (film): $\nu_{max}$=2100 (s, N$_3$), 1700 (s, C=O), 1605 (w), 1585 (w), 1495 (m), 1265 (s), 1235 (s), 1100 (br s, C—O), 1060 (br s, C—O), 735 (br s), 700 (s) cm$^{-1}$.

$^1$H-NMR (500 MHz, CDCl$_3$): δ=7.39-7.22 (25H, m), 4.96 (1H, d, J=12 Hz), 4.91 (1H, d, J=3.5 Hz), 4.87 (1H, d, J=12 Hz), 4.79 (1H, d, J=12 Hz), 4.74 (1H, d, J=12 Hz), 4.68 (1H, d, J=12 Hz), 4.63 (1H, d, J=12 Hz), 4.61 (1H, d, J=12 Hz), 4.57 (1H, d, J=12 Hz), 4.49 (1H, d, J=12 Hz), 4.16-4.06 (3H, m), 3.99 (1H, dd, J=10, 2.5 Hz), 3.98-3.92 (2H, m), 3.85 (1H, br s), 3.76-3.65 (3H, m), 3.63-3.60 (1H, m), 3.43-3.17 (4H, m), 1.71-1.63 (1H, m), 1.58-1.22 (31H, m), 0.88 (3H, t, J=7.0 Hz) ppm.

HR-ESIMS: Calcd for [M+Na]$^+$ ($C_{65}H_{86}N_4O_9Na$): 1089.6293. found: 1089.6301.

Synthesis and Purification Method of RCAI-121

By a method similar to that of conversion of compound 10 to RCAI-123, compound RCAI-121 was synthesized and purified from compound 1'.

The physical properties of RCAI-121 are shown below.

Mp 126-128° C.

$[α]_D^{27}$=+45.0 (c=0.30, pyridine).

IR (KBr): $\nu_{max}$=3380 (br s, OH, NH), 1685 (br s, C=O), 1645 (br s, C=O), 1540 (br m), 1265 (m), 1240 (m), 1150 (br m, C—O), 1080 (br s, C—O), 1040 (br m, C—O), 720 (br m) cm$^{-1}$.

$^1$H-NMR (500 MHz, pyridine-$d_5$): δ=8.49 (1H, d, J=8.5 Hz), 5.52 (1H, d, J=4.0 Hz), 5.29-5.24 (1H, m), 4.86 (1H, dd, J=11, 7.5 Hz), 4.79 (1H, dd, J=11, 5.0 Hz), 4.65 (1H, dd, J=11, 5.5 Hz), 4.60 (1H, dd, J=9.5, 4.0 Hz), 4.49 (1H, dd, J=7.0, 5.5 Hz), 4.37-4.27 (4H, m), 4.35 (1H, dd, J=7.0, 4.0 Hz), 3.43 (4H, br s), 2.50-2.40 (2H, m), 2.32-2.24 (1H, m), 1.97-1.85 (2H, m), 1.82 (2H, dquint., J=7.5, 3.0 Hz), 1.72-1.63 (1H, m), 1.58-1.18 (72H, m), 0.85 (6H, t, J=7.0 Hz) ppm.

HR-ESIMS: Calcd for [M+Na]$^+$ ($C_{56}H_{108}N_2O_{10}Na$): 991.7902. found: 991.7896.

Example 8

Synthesis and Purification Method of RCAI-122 (Compound H)

By a method similar to that in Example 7, RCAI-122 was synthesized and purified.

The physical properties of RCAI-122 are shown below.

Mp 149-152° C.

$[α]_D^{27}$=+43.8 (c=0.33, pyridine).

IR (KBr): $\nu_{max}$=3300 (br s, OH, NH), 1690 (br s, C=O), 1640 (br s, C=O), 1540 (br m), 1250 (br m), 1080 (br s, C—O), 1040 (br m, C—O), 865 (m) cm$^{-1}$.

$^1$H-NMR (500 MHz, pyridine-$d_5$): δ=8.48 (1H, d, J=8.5 Hz), 5.52 (1H, d, J=4.0 Hz), 5.26-5.21 (1H, m), 4.90 (1H, dd, J=11, 8.0 Hz), 4.77 (1H, dd, J=11, 4.5 Hz), 4.65 (1H, dd, J=11, 5.0 Hz), 4.60 (1H, dd, J=10, 4.5 Hz), 4.50 (1H, dd, J=8.0, 5.0 Hz), 4.38 (1H, dd, J=9.5, 3.5 Hz), 4.38-4.34 (1H, m), 4.32-4.26 (2H, m), 4.31 (1H, dd, J=11, 5.0 Hz), 2.48-2.39 (2H, m), 2.30-2.23 (1H, m), 1.96-1.85 (2H, m), 1.81

(2H, dquint., J=7.5, 3.5 Hz), 1.73-1.63 (1H, m), 1.47-1.16 (66H, m), 0.849 (3H, t, J=7.0 Hz), 0.847 (3H, t, J=7.0 Hz) ppm.

HR-ESIMS: Calcd for [M+Na]$^+$ ($C_{55}H_{106}N_2O_{11}Na$): 993.7694. found: 993.7693.

Example 9

Synthesis and Purification Method of RCAI-131 (Compound I)

By a method similar to that in Example 7, RCAI-131 was synthesized and purified.

The physical properties of RCAI-131 are shown below.
Mp 119-120° C.
$[\alpha]_D^{27}$=+41.1 (c=0.32, pyridine).
IR (KBr): $\nu_{max}$=3340 (br s, OH, NH), 1685 (br s, C=O), 1645 (br s, C=O), 1540 (br m), 1080 (br s, C—O), 1040 (br s, C—O), 720 (m) cm$^{-1}$.

$^1$H-NMR (500 MHz, pyridine-d$_5$): δ=8.50 (1H, d, J=8.5 Hz), 5.52 (1H, d, J=3.5 Hz), 5.28-5.23 (1H, m), 4.86 (1H, dd, J=11, 7.0 Hz), 4.79 (1H, dd, J=11, 4.5 Hz), 4.67 (1H, dd, J=10, 5.0 Hz), 4.63-4.59 (1H, m), 4.51 (1H, br t, J=6.0 Hz), 4.39-4.27 (5H, m), 3.42-3.27 (4H, m), 2.58-2.38 (2H, m), 2.31-2.24 (1H, m), 1.96-1.86 (2H, m), 1.81 (2H, dquint., J=7.5, 3.5 Hz), 1.72-1.63 (1H, m), 1.63-1.30 (4H, m), 1.46-1.16 (66H, m), 0.85 (6H, t, J=7.0 Hz) ppm.

HR-ESIMS: Calcd for [M+Na]$^+$ ($C_{55}H_{106}N_2O_{10}Na$): 977.7745. found: 977.7779.

Example 10

Synthesis and Purification Method of RCAI-132 (Compound J)

By a method similar to that in Example 7, RCAI-132 was synthesized and purified.

The physical properties of RCAI-132 are shown below.
Mp 149-151° C.
$[\alpha]_D^{26}$=+41.7 (c=0.31, pyridine).
IR (KBr): $\nu_{max}$=3340 (br s, OH, NH), 1710 (br s, C=O), 1645 (br s, C=O), 1605 (w), 1545 (br s), 1505 (w), 1240 (br m), 1150 (br m, C—O), 1070 (br s, C—O), 720 (w) cm$^{-1}$.

$^1$H-NMR (500 MHz, pyridine-d$_5$): δ=10.56 (1H, s), 8.51 (1H, d, J=8.5 Hz), 7.96 (2H, br d, J=7.5 Hz), 7.36 (2H, t, J=7.5 Hz), 7.06 (1H, t, J=7.5 Hz), 5.49 (1H, d, J=3.5 Hz), 5.19-5.14 (1H, m), 5.00 (1H, dd, J=11, 8.0 Hz), 4.78 (1H, dd, J=11, 4.0 Hz), 4.62-4.56 (1H, m), 4.61 (1H, dd, J=11, 5.5 Hz), 4.57 (1H, dd, J=8.0, 4.0 Hz), 4.38-4.30 (4H, m), 4.30-4.24 (1H, m), 2.43 (2H, dt, J=7.0 Hz), 2.27-2.20 (1H, m), 1.97-1.86 (2H, m), 1.84-1.74 (2H, m), 1.71-1.62 (1H, m), 1.46-1.16 (66H, m), 0.853 (3H, t, J=7.0 Hz), 0.849 (3H, t, J=7.0 Hz) ppm.

HR-ESIMS: Calcd for [M+Na]$^+$ ($C_{57}H_{104}N_2O_{10}Na$): 999.7589. found: 999.7600.

Example 11

Synthesis and Purification Method of RCAI-139 (Compound K)

By a method similar to that in Example 7, RCAI-139 was synthesized and purified.

The physical properties of RCAI-139 are shown below.
Mp 154-156° C.
$[\alpha]_D^{26}$=+42.2 (c=0.31, pyridine).
IR (KBr): $\nu_{max}$=3360 (br s, OH, NH), 1705 (br s, C=O), 1665 (br s, C=O), 1530 (br s), 1250 (s), 1150 (m, C—O), 1070 (br s, C—O), 830 (m), 760 (m) cm$^{-1}$.

$^1$H-NMR (500 MHz, pyridine-d$_5$): δ=10.44 (1H, s), 8.55 (1H, d, J=8.0 Hz), 7.88 (2H, br d, J=7.0 Hz), 7.00 (2H, d, J=9.0 Hz), 5.50 (1H, d, J=4.0 Hz), 5.21-5.15 (1H, m), 5.01 (1H, dd, J=12, 8.0 Hz), 4.80 (1H, dd, J=12, 4.0 Hz), 4.64-4.56 (3H, m), 4.38-4.31 (4H, m), 4.27 (1H, br t, J=7.0 Hz), 3.65 (3H, s), 2.44 (2H, dt, J=7.0, 2.0 Hz), 2.28-2.21 (1H, m), 1.96-1.85 (2H, m), 1.85-1.75 (2H, m), 1.71-1.62 (1H, m), 1.46-1.16 (66H, m), 0.849 (3H, t, J=7.0 Hz), 0.846 (3H, t, J=7.0 Hz) ppm.

HR-ESIMS: Calcd for [M+Na]$^+$ ($C_{58}H_{106}N_2O_{11}Na$): 1029.7694. found: 1029.7670.

Example 12

Synthesis and Purification Method of RCAI-140 (Compound L)

By a method similar to that in Example 7, RCAI-140 was synthesized and purified.

The physical properties of RCAI-140 are shown below.
Mp 149-150° C.
$[\alpha]_D^{27}$=+39.4 (c=0.31, pyridine).
IR (KBr): $\nu_{max}$=3320 (br s, OH, NH), 1710 (br s, C=O), 1645 (br s, C=O), 1545 (br s), 1240 (br m), 1075 (br s, C—O), 1040 (m, C—O), 820 (m) cm$^{-1}$.

$^1$H-NMR (500 MHz, pyridine-d$_5$): δ=10.49 (1H, s), 8.56 (1H, d, J=8.0 Hz), 7.87 (2H, br d, J=7.0 Hz), 7.16 (2H, d, J=8.5 Hz), 5.49 (1H, d, J=3.5 Hz), 5.20-5.14 (1H, m), 5.00 (1H, dd, J=11, 7.5 Hz), 4.78 (1H, dd, J=11, 4.0 Hz), 4.64-4.56 (3H, m), 4.39-4.31 (4H, m), 4.27 (1H, br t, J=6.5 Hz), 2.44 (2H, t, J=7.0 Hz), 2.27-2.17 (1H, m), 2.20 (3H, s), 1.96-1.85 (2H, m), 1.85-1.74 (2H, m), 1.71-1.62 (1H, m), 1.46-1.16 (66H, m), 0.849 (3H, t, J=7.0 Hz), 0.846 (3H, t, J=7.0 Hz) ppm.

HR-ESIMS: Calcd for [M+Na]$^+$ ($C_{58}H_{106}N_2O_{10}Na$): 1013.7745. found: 1013.7739.

Example 13

Synthesis and Purification Method of RCAI-141 (Compound M)

By a method similar to that in Example 7, RCAI-141 was synthesized and purified.

The physical properties of RCAI-141 are shown below.
Mp 163-165° C.
$[\alpha]_D^{29}$=+36.1 (c=0.30, pyridine).
IR (KBr): $\nu_{max}$=3400 (br s, OH), 3300 (br m, NH), 1710 (br s, C=O), 1640 (br s, C=O), 1620 (br s, C=O), 1545 (br s), 1330 (s), 1245 (br m), 1165 (m, C—O), 1130 (br s, C—O), 1070 (br s, C—O), 840 (m) cm$^{-1}$.

$^1$H-NMR (500 MHz, pyridine-d$_5$): δ=10.97 (1H, s), 8.60 (1H, d, J=8.5 Hz), 8.03 (2H, d, J=8.5 Hz), 7.65 (2H, d, J=8.5 Hz), 5.50 (1H, d, J=4.0 Hz), 5.18-5.13 (1H, m), 5.03 (1H, dd, J=11, 8.5 Hz), 4.78 (1H, dd, J=11, 3.5 Hz), 4.61 (1H, dd, J=9.5, 3.5 Hz), 4.61-4.58 (2H, m), 4.40-4.32 (4H, m), 4.26 (1H, dd, J=8.5, 2.5 Hz), 2.44 (2H, t, J=7.0 Hz), 2.26-2.19 (1H, m), 1.95-1.85 (2H, m), 1.83-1.73 (2H, m), 1.71-1.61 (1H, m), 1.46-1.16 (66H, m), 0.849 (3H, t, J=7.0 Hz), 0.845 (3H, t, J=7.0 Hz) ppm.

HR-ESIMS: Calcd for [M+Na]$^+$ ($C_{58}H_{103}N_2O_{10}F_3Na$): 1067.7463. found: 1067.7469.

Example 14

Synthesis and Purification Method of RCAI-150 (Encompassed in Compound N)

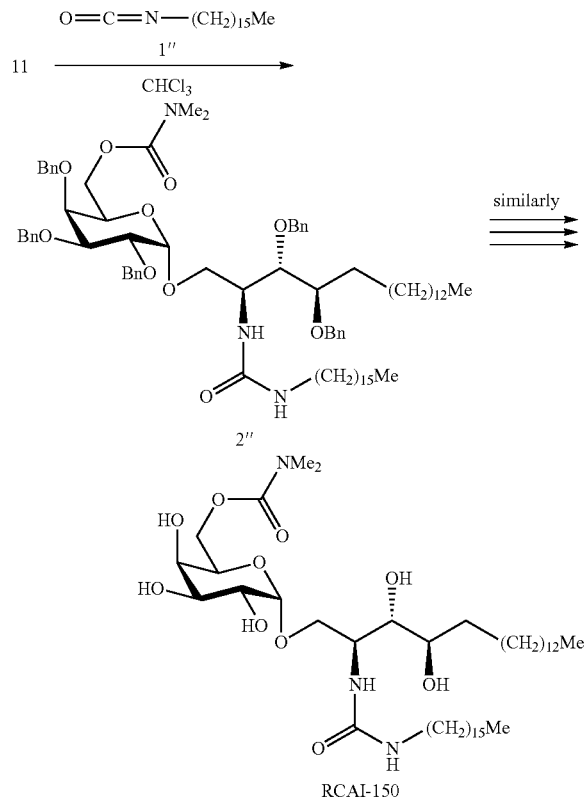

Synthesis of Compound 2″

To a solution of compound 11 (119 mg, 0.119 mmol) obtained by the above-mentioned process in chloroform (5 mL) was added commercially available hexadecylisocyanate (compound 1″, 111 μL, 0.357 mmol) at 0° C. The reaction mixture was stirred at room temperature for 14 hr, water was added, and the mixture was extracted with ethyl acetate. The organic layer was successively washed with water, saturated aqueous sodium hydrogen carbonate solution and saturated brine, and dried over anhydrous magnesium sulfate. After filtration, the filtrate was concentrated under reduced pressure, and the solvent was evaporated. The residue was purified by silica gel column chromatography (30 g, hexane:ethyl acetate=3:1) to give compound 2″ (147 mg, 97%) as a colorless solid.

Mp 79.5-81.0° C.

$[\alpha]_D^{26}$=+21.3 (c=1.02, CHCl$_3$).

IR (KBr): $\nu_{max}$=3420 (m, NH), 3340 (m, NH), 1710 (s, C=O), 1650 (s, C=O), 1545 (s), 1495 (m), 1290 (m), 1190 (br s, C—O), 1100 (br s, C—O), 1060 (br s, C—O), 740 (br s), 695 (s) $^1$H-NMR (500 MHz, CDCl$_3$): δ=7.39-7.15 (25H, m), 5.13 (1H, br s), 4.98 (1H, d, J=12 Hz), 4.90 (1H, br d, J=9.0 Hz), 4.84 (1H, d, J=12 Hz), 4.81 (1H, d, J=4.0 Hz), 4.78 (1H, d, J=12 Hz), 4.74 (1H, d, J=12 Hz), 4.73 (1H, d, J=12 Hz), 4.68 (1H, d, J=12 Hz), 4.62 (1H, d, J=12 Hz), 4.58 (1H, d, J=12 Hz), 4.57 (1H, d, J=12 Hz), 4.48 (1H, d, J=12 Hz), 4.17 (1H, dd, J=11, 5.0 Hz), 4.09-4.03 (3H, m), 3.99 (1H, br t, J=6.5 Hz), 3.96-3.88 (1H, m), 3.90 (1H, dd, J=10, 3.0 Hz), 3.86 (1H, br s), 3.74 (1H, dd, J=8.0, 3.0 Hz), 3.68 (1H, dd, J=11, 3.0 Hz), 3.59 (1H, dt, J=8.0, 3.0 Hz), 3.07-3.01 (2H, m), 2.84 (3H, s), 2.73 (3H, s), 1.72-1.53 (3H, m), 1.50-1.40 (1H, m), 1.40-1.18 (52H, m), 0.88 (6H, t, J=7.0 Hz) ppm.

HR-ESIMS: Calcd for [M+Na]$^+$ (C$_{79}$H$_{147}$N$_3$O$_{10}$Na) 1290.8637. found: 1290.8606.

Synthesis and Purification Method of RCAI-150

By a method similar to that of conversion of compound 13 to RCAI-123, RCAI-150 was synthesized and purified from compound 2″.

The physical properties of compound RCAI-150 are shown below.

Mp 140-142° C.

$[\alpha]_D^{27}$=+52.8 (c=0.32, pyridine).

IR (KBr): $\nu_{max}$=3480 (br s), 3440 (br m), 3350 (br s), 1690 (s, C=O), 1670 (s, C=O), 1620 (s, C=O), 1590 (br m), 1215 (m), 1080 (br s, C—O) cm$^{-1}$.

$^1$H-NMR (500 MHz, pyridine-d$_5$): δ=6.79 (1H, t, J=5.5 Hz). 6.70 (1H, d, J=9.0 Hz), 5.51 (1H, d, J=4.0 Hz), 5.12-5.08 (1H, m), 4.81 (1H, dd, J=11, 7.5 Hz), 4.71 (1H, dd, J=11, 5.0 Hz), 4.61 (1H, dd, J=10, 5.0 Hz), 4.57 (1H, dd, J=9.0, 3.5 Hz), 4.41 (1H, dd, J=7.0, 5.0 Hz), 4.36 (1H, dd, J=10, 3.5 Hz), 4.30-4.22 (4H, m), 3.52-3.39 (2H, m), 2.81 (6H, br s), 2.30-2.22 (1H, m), 1.92-1.80 (2H, m), 1.68-1.60 (1H, m), 1.57 (2H, quint., J=7.0 Hz), 1.44-1.16 (48H, m), 0.85 (6H, t, J=7.0 Hz) ppm.

HR-ESIMS: Calcd for [M+Na]$^+$ (C$_{44}$H$_{87}$N$_3$O$_{10}$Na): 840.6289. found: 840.6276.

Experimental Example 1

Biological Activity Test of Carbamate Glycolipid

Solutions of each of α-GalCer (KRN7000), RCAI-123, RCAI-124, RCAI-137, RCAI-138, RCAI-148, RCAI-149, RCAI-121, RCAI-122, RCAI-131, RCAI-132, RCAI-139, RCAI-140, RCAI-141 and RCAI-150 in dimethyl sulfoxide (DMSO) at a concentration of 1 mg/mL were prepared. The above-mentioned DMSO solutions were diluted 5-fold with 0.5% tween 20 (Bio-Rad)-containing phosphate buffer (Invitrogen) and further diluted 20-fold with phosphate buffer, such that the dose became 100 μg/kg body weight when 200 μL was administered per mouse from the tail vein.

To three C57BL/6 mice per group was injected each prepared solution (200 μL) of RCAI-123, RCAI-124, RCAI-137, RCAI-138, RCAI-148, RCAI-149, RCAI-121, RCAI-122, RCAI-131, RCAI-132, RCAI-139, RCAI-140, RCAI-141 or RCAI-150 into the tail vein (administration of about 2 μg per mouse). As a control substance, α-GalCer (KRN7000) was used, and a solution (200 μL) of α-GalCer (KRN7000) prepared in the same manner such that the dose became 100 μg/kg body weight was injected into the tail vein. The blood (80 μL) immediately before administration, and after lapse of 1, 3, 6, 12, 24, 32, 48, 60 and 72 hr was collected from orbital plexus venosus, and plasma was prepared.

The content of each cytokine in plasma immediately before and after administration of RCAI-123 was measured by Cytometric Bead Array (CBA) system (BD Biosciences) which is one of the ELISA methods.

Figure 2:
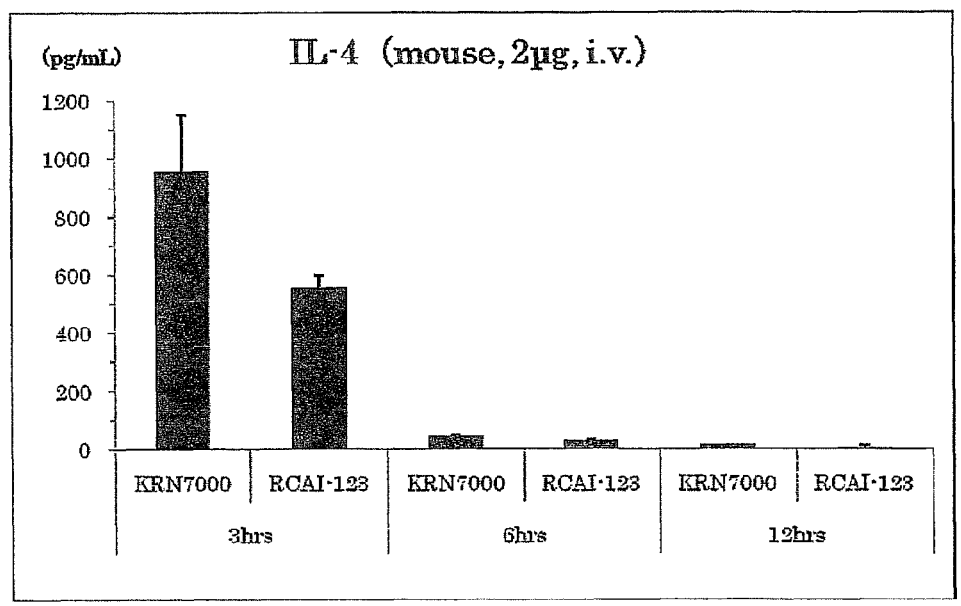
FIG. 2 is a graph showing changes in the IL-4 concentration of mouse plasma after lapse of an indicated time after intravenous administration of a glycolipid (KRN7000 or RCAI-123) to mouse.
Figure 3:
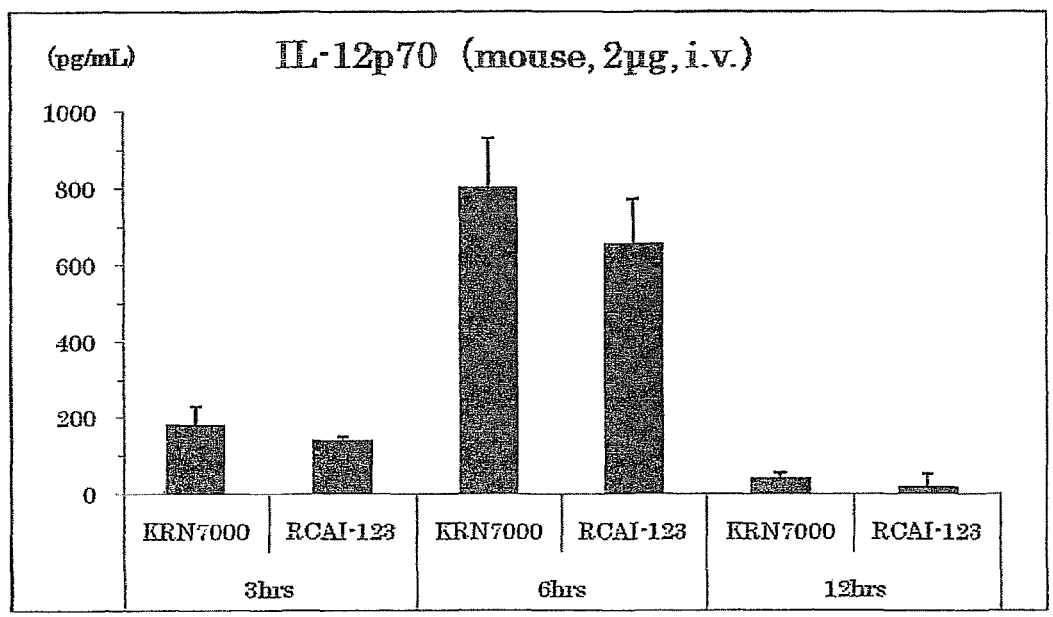
FIG. 3 is a graph showing changes in the IL-12 concentration of mouse plasma after lapse of an indicated time after intravenous administration of a glycolipid (KRN7000 or RCAI-123) to mouse.

The measurement results (mean) and standard deviation thereof (STDEV) of the content of IFN-γ in plasma immediately before administration, and after lapse of 1, 3, 6, 12, 24, 32, 48, 60 and 72 hr are shown in FIG. 1. The measurement results (mean) and standard deviation thereof (STDEV) of the content of IL-4 in plasma immediately before administration, and after lapse of 3, 6 and 12 hr from the administration are shown in FIG. 2. The measurement results (mean) and standard deviation thereof (STDEV) of the content of IL-12 in plasma immediately before administration, and after lapse of 3, 6 and 12 hr from the administration are shown in FIG. 3.

The above-mentioned results reveal that RCAI-123 induced IFN-γ production to the same degree as α-GalCer (KRN7000), but induced a small amount of IL-4 production as compared to α-GalCer (KRN7000), which indicates that RCAI-123 has a cytokine production induction activity biased toward IFN-γ. That is, by converting the 6-position hydroxyl group of the sugar moiety to a carbamate bond, a novel compound capable of inducing cytokine production biased toward Th1 type has been developed.

Experimental Example 2

Biological Activity Test of Dendritic Cells Pulsed with Carbamate Glycolipid (Preparation of Dendritic Cells)

Bone marrow cells were collected from the femur of C57BL/6J mouse, hemolyzed with red blood cell lysing buffer (SIGMA), and mononuclear cells were prepared. Furthermore, Fcγ receptor positive cells were removed according to a panning method using human γ-globulin (SIGMA) to concentrate the undifferentiated cells.

The concentrated undifferentiated mononuclear cells at a density of $2.7 \times 10^5/cm^2$ were cultivated in RPMI1640 (10% FBS) medium (Invitrogen) containing 5 ng/mL GM-CSF (R&D) under conditions of 37° C., 5% $CO_2$ for 5 days to induce differentiation into cells containing CD11c-positive dendritic cells.

To recover the object CD11c-positive dendritic cells from the differentiation-induced cells, the cells were suspended in 400 μL RPMI1640 (10% FBS), 100 μL CD11c microbeads (Milltenyi biotech) were added, and the mixture was incubated at 4° C. for 15 min. The mixture was washed with MACS buffer and CD11c-positive dendritic cells were recovered by positive selection using LS column.

The recovered dendritic cells were pulsed with glycolipid by culture at a density of $3.1 \times 10^5/cm^2$ in RPMI1640 (10% FBS) medium containing glycolipid at a concentration of 100 ng/mL under the conditions of 37° C., 5% $CO_2$ for 24 hr. For preparation of a glycolipid solution, a dimethyl sulfoxide (DMSO) solution at a concentration of 1 mg/mL was prepared first. The solution was diluted 5-fold with phosphate buffer (Invitrogen) containing 0.5% tween 20 (Bio-Rad), and further diluted 2-fold with phosphate buffer.

The dendritic cells pulsed with glycolipid were washed with phosphate buffer, adjusted to a concentration of $2.5 \times 10^6$ cells/mL with phosphate buffer, and 200 μL, i.e., $5 \times 10^5$ cells, was injected into the tail vein of C57BL/6 mouse (three mice per group).

As the glycolipid, carbamate glycolipids of RCAI-121, RCAI-122, RCAI-123, RCAI-124, RCAI-131, RCAI-132, RCAI-137, RCAI-138, RCAI-139, RCAI-140 and RCAI-141 were used, and α-GalCer (KRN7000) was used as a control substance.

The blood (80 μL) was collected from orbital plexus venosus immediately before administration, and after lapse of 1, 3, 6, 12, 24, 32, 48, 60 and 72 hr from the administration, and plasma was prepared.

Figure 4:
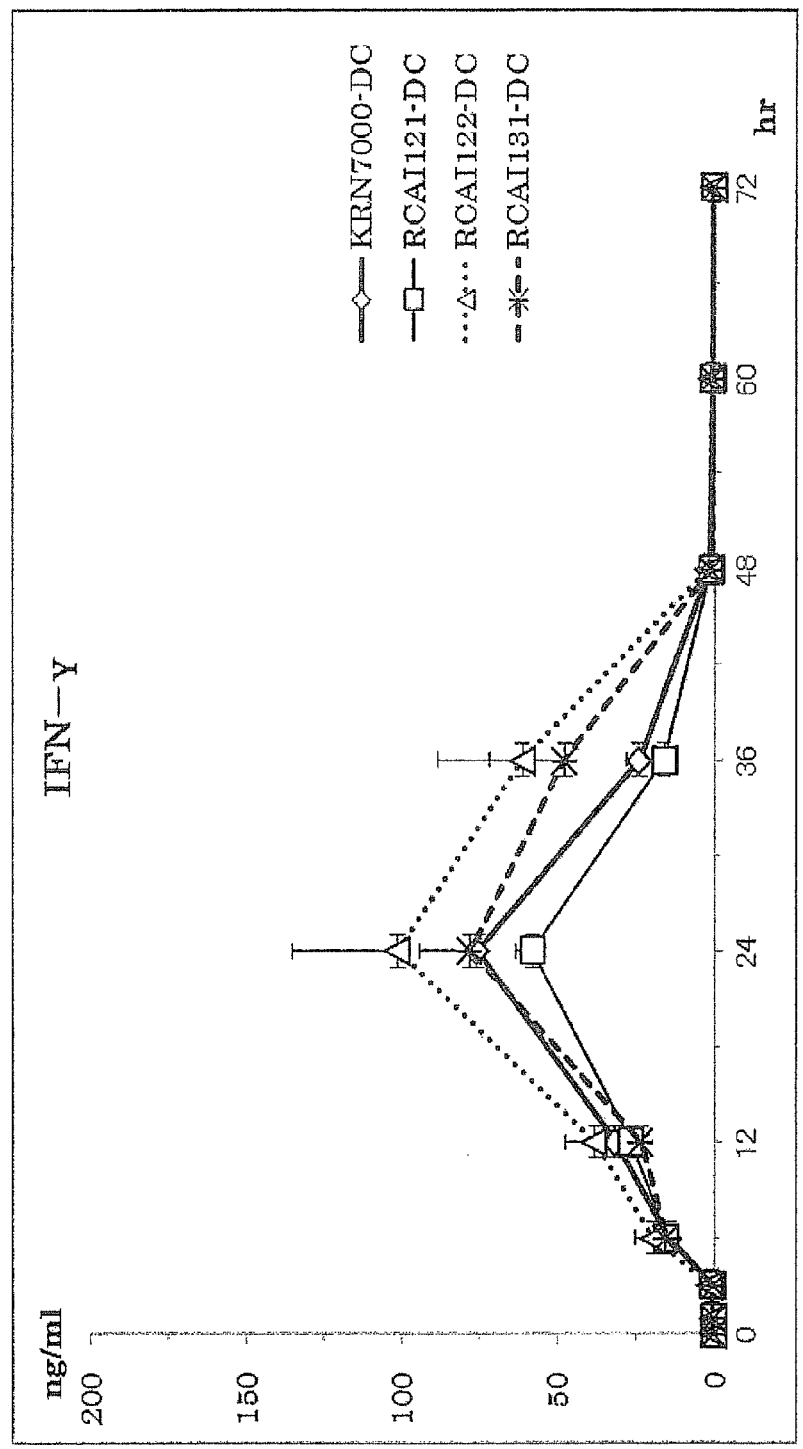
FIG. 4 is a graph showing changes in the IFN-γ concentration of mouse plasma after lapse of an indicated time after intravenous administration of dendritic cells pulsed with a glycolipid (KRN7000 or RCAI-121, RCAI-122, RCAI-131) to mouse.
Figure 5:
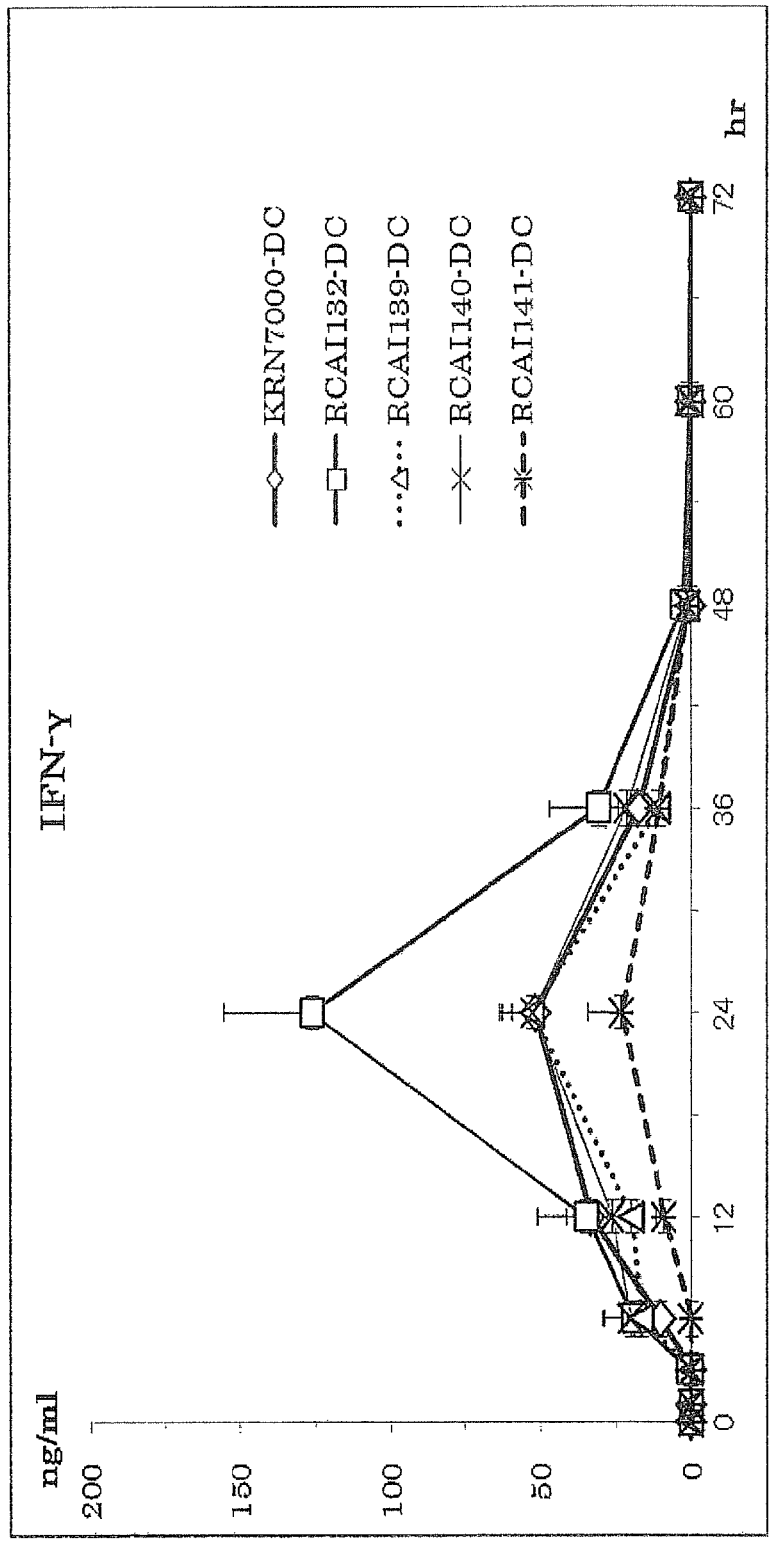
FIG. 5 is a graph showing changes in the IFN-γ concentration of mouse plasma after lapse of an indicated time after intravenous administration of dendritic cells pulsed with a glycolipid (KRN7000 or RCAI-132, RCAI-139, RCAI-140, RCAI-141) to mouse.
Figure 6:
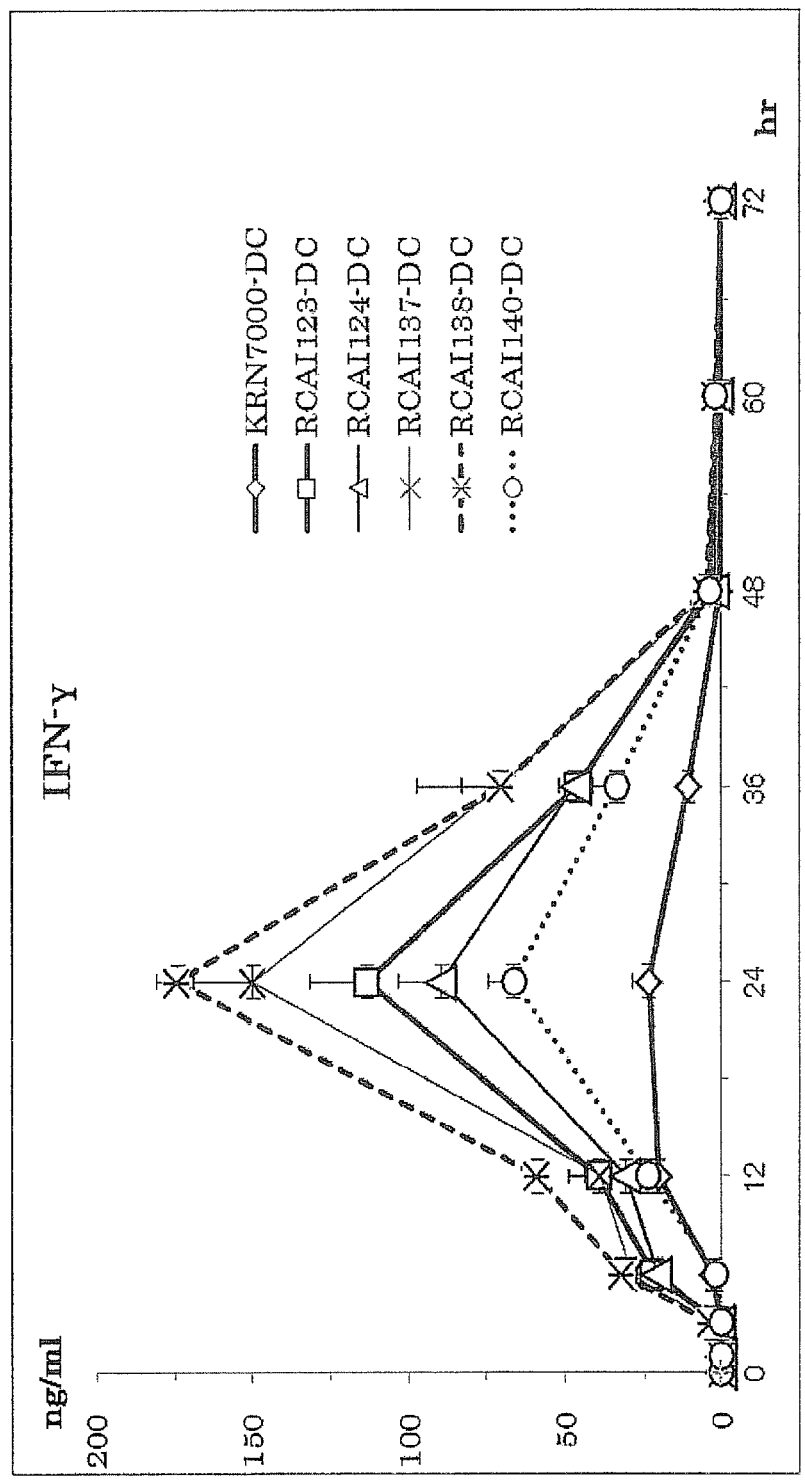
FIG. 6 is a graph showing changes in the IFN-γ concentration of mouse plasma after lapse of an indicated time after intravenous administration of dendritic cells pulsed with a glycolipid (KRN7000 or RCAI-123, RCAI-124, RCAI-137, RCAI-138, RCAI-140) to mouse.

The content of IFN-γ in plasma immediately before administration, and after lapse of 1, 3, 6, 12, 24, 32, 48, 60 and 72 hr from the administration was measured by sandwich ELISA method (ENDOGEN). The measurement results (mean) of the production amount of IFN-γ and the standard deviation thereof (STDEV) are shown in FIGS. 4-6.

Figure 7:
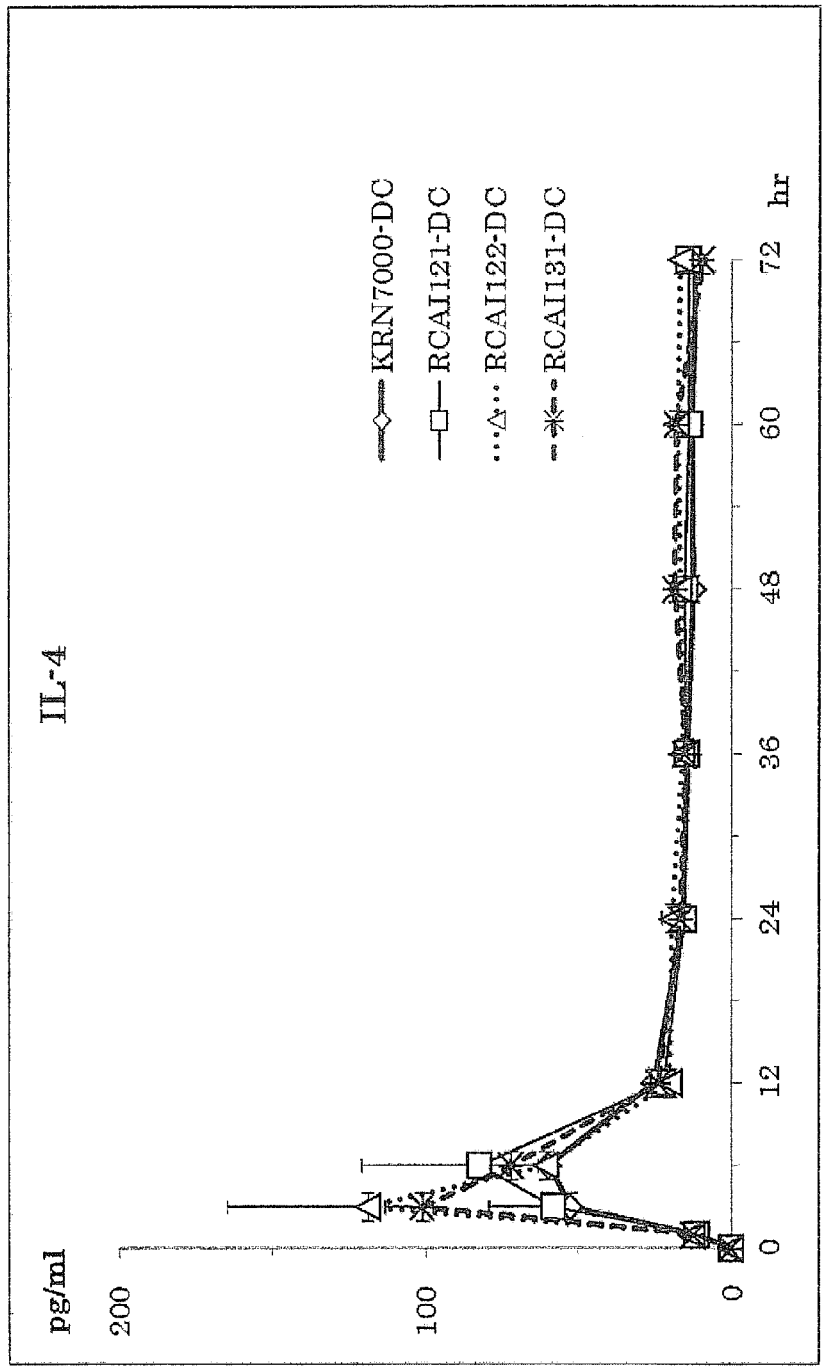
FIG. 7 is a graph showing changes in the IL-4 concentration of mouse plasma after lapse of an indicated time after intravenous administration of dendritic cells pulsed with a glycolipid (KRN7000 or RCAI-121, RCAI-122, RCAI-131) to mouse.
Figure 8:
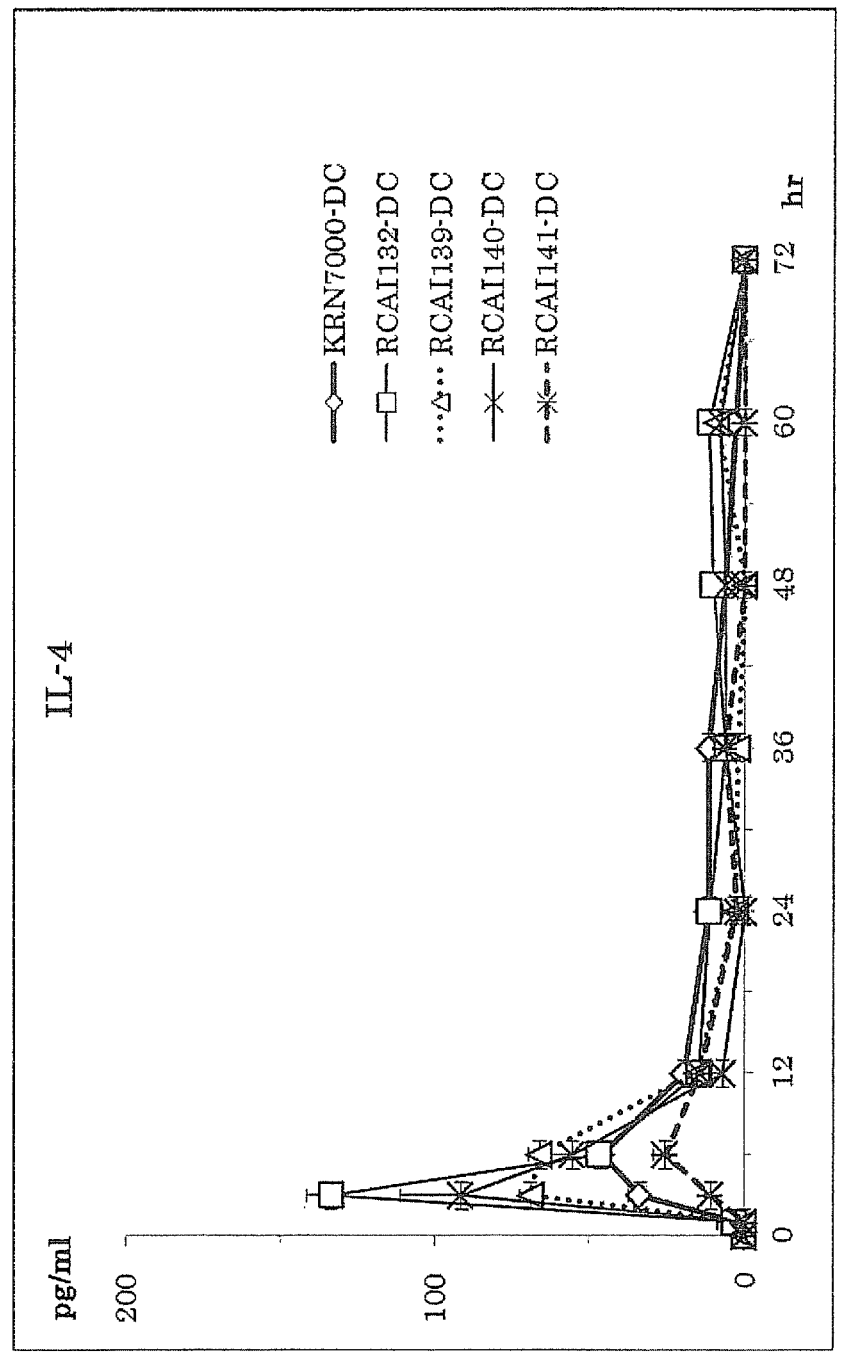
FIG. 8 is a graph showing changes in the IL-4 concentration of mouse plasma after lapse of an indicated time after intravenous administration of dendritic cells pulsed with a glycolipid (KRN7000 or RCAI-132, RCAI-139, RCAI-140, RCAI-141) to mouse.
Figure 9:
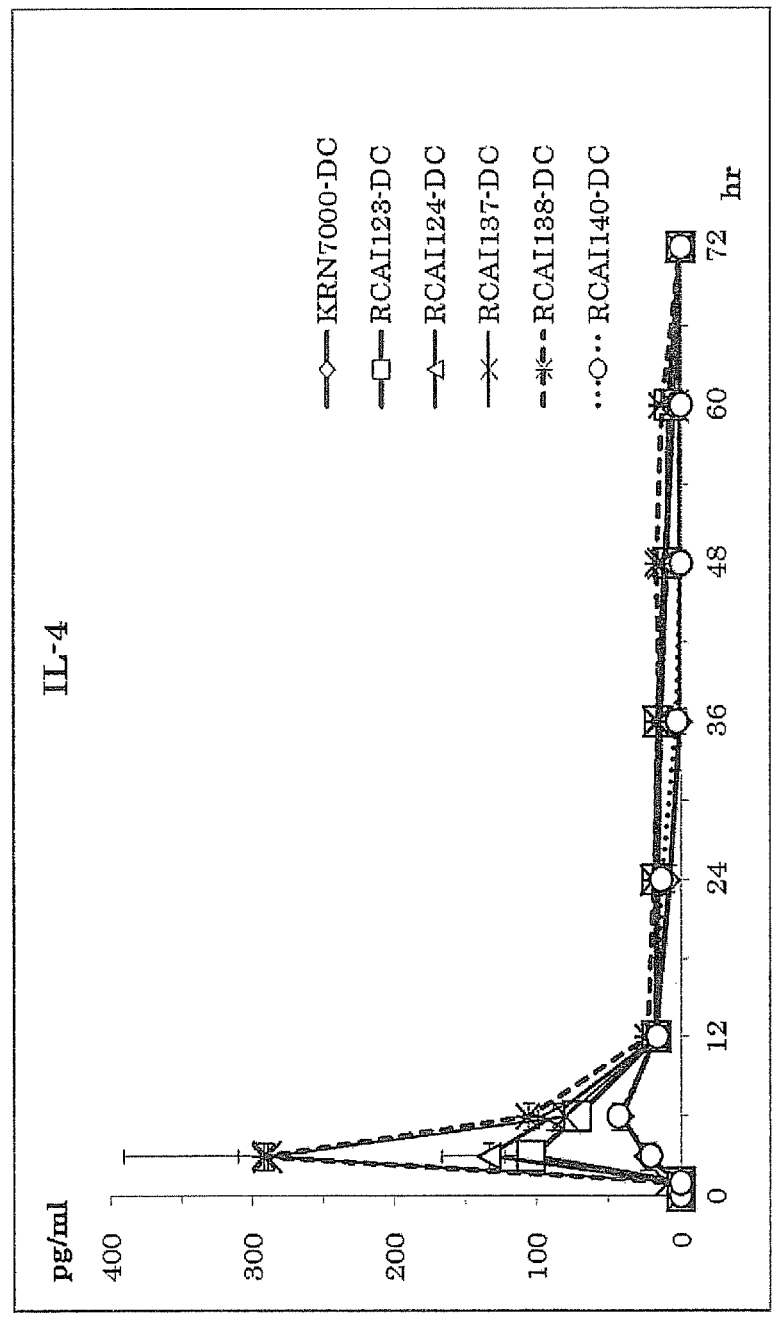
FIG. 9 is a graph showing changes in the IL-4 concentration of mouse plasma after lapse of an indicated time after intravenous administration of dendritic cells pulsed with a glycolipid (KRN7000 or RCAI-123, RCAI-124, RCAI-137, RCAI-138, RCAI-140) to mouse.

The content of IL-4 in plasma immediately before administration, and after lapse of 1, 3, 6, 12, 24, 32, 48, 60 and 72 hr from the administration was measured by Cytometric Bead Array (CBA) system (BD Biosciences) which is one of the ELISA methods. The measurement results (mean) of the production amount of IL-4 and the standard deviation thereof (STDEV) are shown in FIGS. 7-9.

Figure 10:
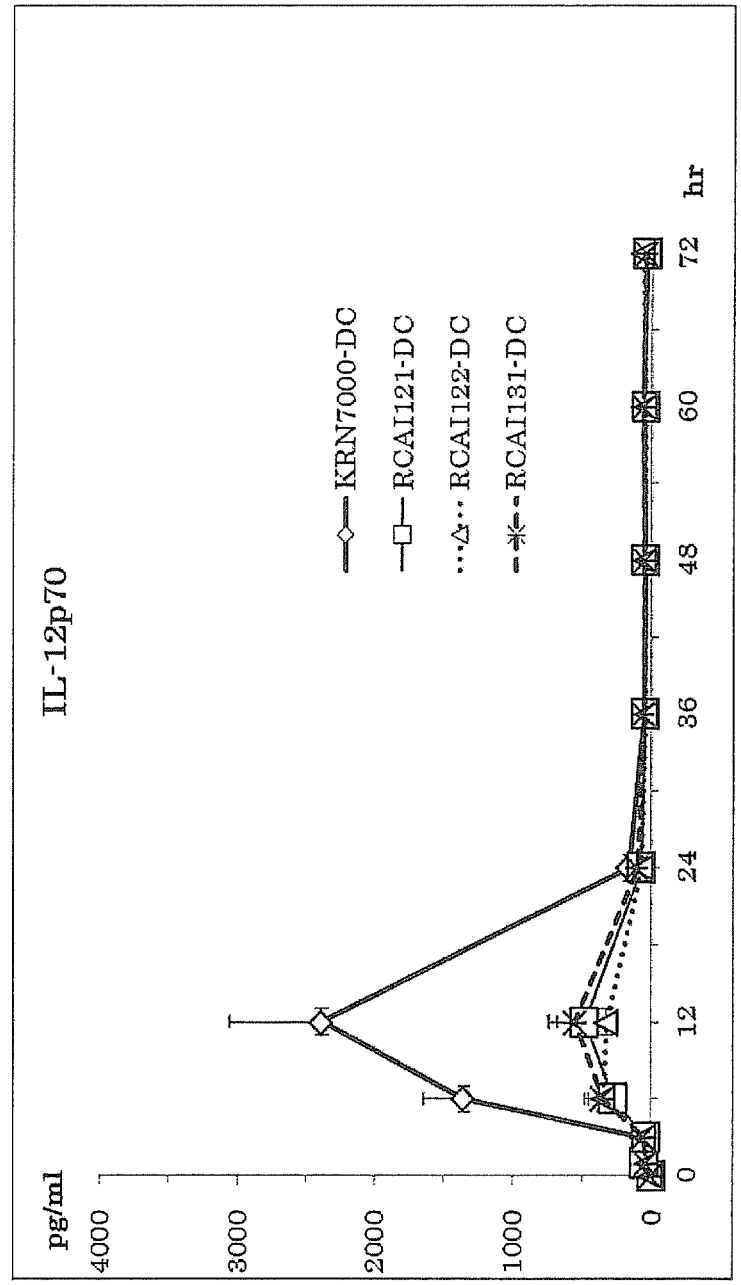
FIG. 10 is a graph showing changes in the IL-12 concentration of mouse plasma after lapse of an indicated time after intravenous administration of dendritic cells pulsed with a glycolipid (KRN7000 or RCAI-121, RCAI-122, RCAI-131) to mouse.
Figure 11:
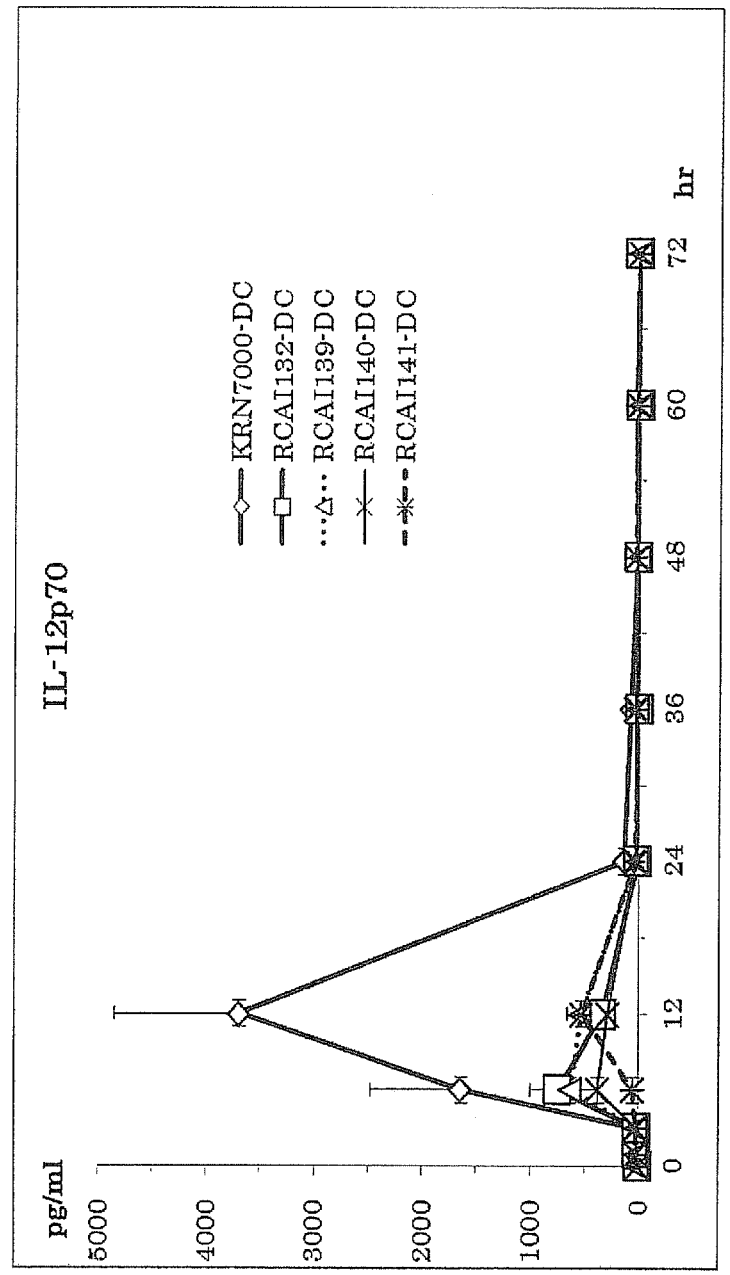
FIG. 11 is a graph showing changes in the IL-12 concentration of mouse plasma after lapse of an indicated time after intravenous administration of dendritic cells pulsed with a glycolipid (KRN7000 or RCAI-132, RCAI-139, RCAI-140, RCAI-141) to mouse.
Figure 12:
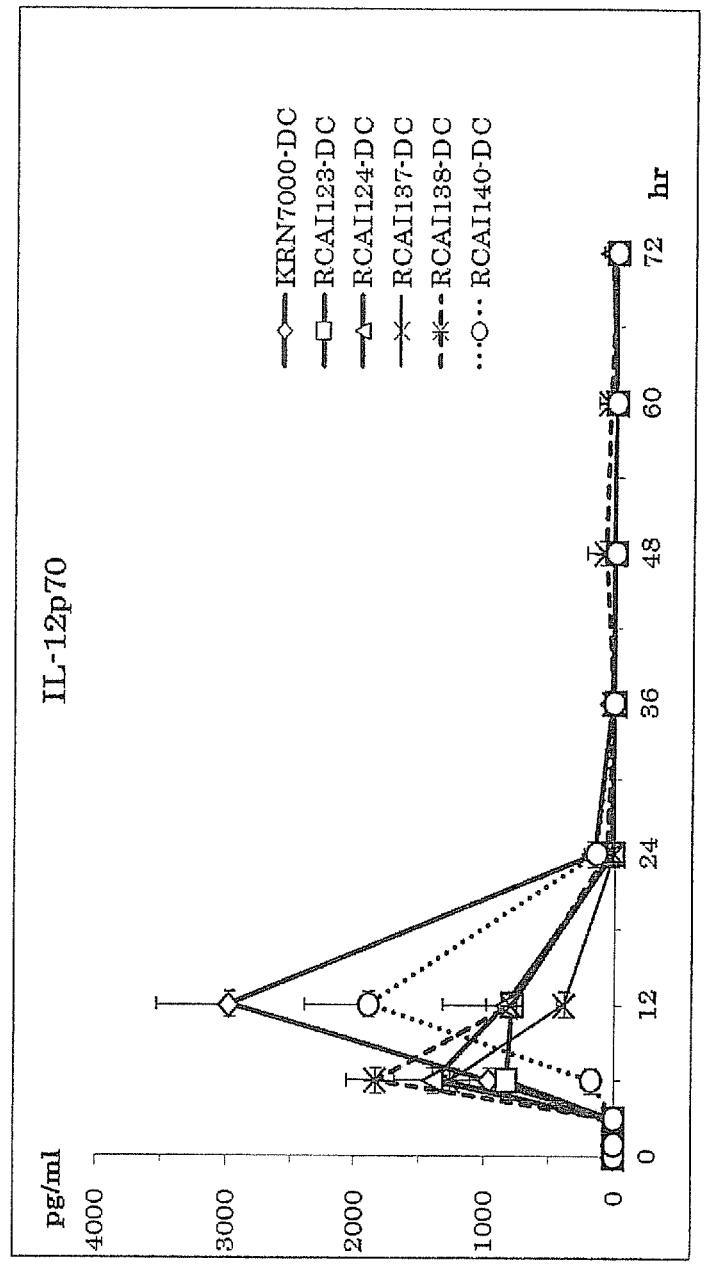
FIG. 12 is a graph showing changes in the IL-12 concentration of mouse plasma after lapse of an indicated time after intravenous administration of dendritic cells pulsed with a glycolipid (KRN7000 or RCAI-123, RCAI-124, RCAI-137, RCAI-138, RCAI-140) to mouse.

The content of IL-12 in plasma immediately before administration, and after lapse of 1, 3, 6, 12, 24, 32, 48, 60 and 72 hr from the administration was measured by CBA system (BD Biosciences). The measurement results (mean) of the production amount of IL-12 and the standard deviation thereof (STDEV) are shown in FIGS. 10-12.

The above-mentioned results reveal that stronger IFN-γ production can be selectively induced by pulsing dendritic cells with the carbamate glycolipid of the present invention and administering the pulsed dendritic cells to the living body.

INDUSTRIAL APPLICABILITY

Since a glycolipid wherein the 6-position hydroxyl group of the sugar moiety is converted to a carbamate bond, which is developed by the present invention, can be synthesized highly easily and capable of inducing IFN-γ polarized cytokine production than KRN7000, the present invention can provide a medicament effective for cancer treatment and induction of adjuvant action, a production method thereof and use thereof.

Furthermore, IFN-γ production can be potentiated more by pulsing dendritic cells with the glycolipid of the present invention and administering the dendritic cells.

This application is based on patent application No. 2012-101384 filed in Japan (filing date: Apr. 26, 2012), the contents of which are incorporated in full herein.

The invention claimed is:

1. A compound represented by the formula (I)

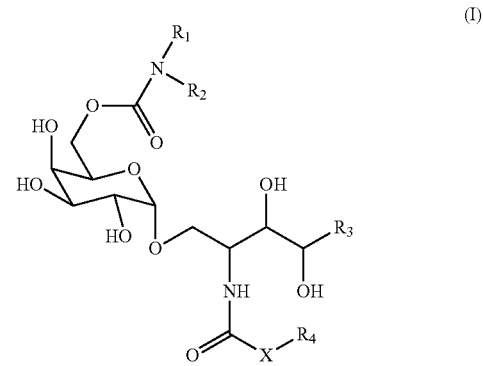

wherein
X is an alkylene group or —NH—;
$R_1$ and $R_2$ are the same or different and each is
  a hydrogen atom,
  an alkyl group,
  a hydroxyl group,
  an alkoxy group, or
  an aryl group optionally having substituent(s), or
$R_1$ and $R_2$ optionally form, together with the adjacent nitrogen atom, a 5- or 6-membered ring;
$R_3$ is a hydrocarbon group having 1-20 carbon atoms; and
$R_4$ is a hydrocarbon group having 1-30 carbon atoms, or a salt thereof.

2. The compound according to claim 1, wherein X is methylene or —NH—, or a salt thereof.

3. The compound according to claim 1, wherein $R_1$ is a hydrogen atom, a $C_{1-6}$ alkyl group, a hydroxyl group, a $C_{1-6}$ alkoxy group, or a $C_{6-12}$ aryl group optionally having substituent(s), or a salt thereof.

4. The compound according to claim 1, wherein $R_2$ is a hydrogen atom, a $C_{1-6}$ alkyl group, a hydroxyl group, a $C_{1-6}$ alkoxy group, or a $C_{6-12}$ aryl group optionally having substituent(s), or a salt thereof.

5. The compound according to claim 1, wherein the 5- or 6-membered ring optionally formed by $R_1$ and $R_2$ together with the adjacent nitrogen atom is a 5- or 6-membered nitrogen-containing saturated heterocycle, or a salt thereof.

6. The compound according to claim 1, wherein $R_3$ is a $C_{1-20}$ alkyl group, a $C_{2-20}$ alkenyl group or a $C_{2-20}$ alkynyl group, or a salt thereof.

7. The compound according to claim 1, wherein $R_4$ is a $C_{1-30}$ alkyl group, a $C_{2-30}$ alkenyl group or a $C_{2-30}$ alkynyl group, or a salt thereof.

8. A medicament comprising the compound according to claim 1, or a salt thereof.

9. A selective IFN-γ production inducer comprising the compound according to claim 1, or a salt thereof.

10. A human dendritic cell pulsed with the compound according to claim 1, or a salt thereof.

11. A selective IFN-γ production inducer comprising the human dendritic cell described in claim 10.

12. A compound represented by the formula (II)

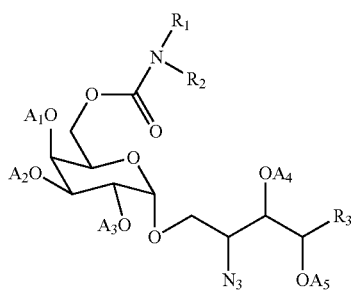

(II)

wherein $A_1$-$A_5$ are the same or different and each is a hydroxyl-protecting group;

$R_1$ and $R_2$ are the same or different and each is a hydrogen atom, an alkyl group, a hydroxyl group, an alkoxy group, or an aryl group optionally having substituent(s), or $R_1$ and $R_2$ optionally form, together with the adjacent nitrogen atom, a 5- or 6-membered ring; and $R_3$ is a hydrocarbon group having 1-20 carbon atoms, or a salt thereof.

13. The compound according to claim 12, wherein $R_1$ and $R_2$ are the same or different and each is a hydrogen atom, a $C_{1-6}$ alkyl group, a hydroxyl group, a $C_{1-6}$ alkoxy group, or a $C_{6-12}$ aryl group optionally having substituent(s), or $R_1$ and $R_2$ optionally form, together with the adjacent nitrogen atom, a 5- or 6-membered nitrogen-containing saturated heterocycle, or a salt thereof.

14. The compound according to claim 12, wherein $R_3$ is a $C_{1-20}$ alkyl group, a $C_{2-20}$ alkenyl group or a $C_{2-20}$ alkynyl group, or a salt thereof.

15. A method of selectively inducing production of IFN-γ, comprising administering an effective amount of the compound according to claim 1, or a salt thereof to a target in need of the administration.

16. A method of selectively inducing production of IFN-γ, comprising administering an effective amount of the compound according to claim 1, or a salt thereof to a target in need of the administration, and a step of pulsing dendritic cells with the compound or a salt thereof.

* * * * *